(12) United States Patent
Van Der Schaar et al.

(10) Patent No.: US 10,437,163 B2
(45) Date of Patent: Oct. 8, 2019

(54) METHOD AND APPARATUS FOR DESIGN OF A METROLOGY TARGET

(71) Applicant: ASML Netherlands B.V., Veldhoven (NL)

(72) Inventors: Maurits Van Der Schaar, Eindhoven (NL); Murat Bozkurt, Uden (NL); Patrick Warnaar, Tilburg (NL); Stefan Cornelis Theodorus Van Der Sanden, Nijmegen (NL)

(73) Assignee: ASML Netherlands B.V., Veldhoven (NL)

(*) Notice: Subject to any disclaimer, the term of this patent is extended or adjusted under 35 U.S.C. 154(b) by 25 days.

(21) Appl. No.: 15/650,401

(22) Filed: Jul. 14, 2017

(65) Prior Publication Data

US 2018/0017881 A1    Jan. 18, 2018

Related U.S. Application Data

(60) Provisional application No. 62/362,812, filed on Jul. 15, 2016, provisional application No. 62/385,615, filed on Sep. 9, 2016.

(51) Int. Cl.
*G03F 9/00* (2006.01)
*G01N 21/956* (2006.01)
*G03F 7/20* (2006.01)

(52) U.S. Cl.
CPC ......... *G03F 9/7046* (2013.01); *G01N 21/956* (2013.01); *G03F 7/70616* (2013.01);
(Continued)

(58) Field of Classification Search
CPC .. G03F 9/7046; G03F 9/7019; G03F 7/70616; G03F 7/70633; G03F 7/70683; G01N 21/956
See application file for complete search history.

(56) References Cited

U.S. PATENT DOCUMENTS 7,587,704 B2   9/2009 Ye et al.
2006/0033921 A1   2/2006 Den Boef et al.
(Continued)

FOREIGN PATENT DOCUMENTS

WO   WO 2013/143814 A1   10/2013
WO   WO 2015/018625 A1   2/2015
(Continued)

OTHER PUBLICATIONS

International Search Report and Written Opinion of the International Searching Authority directed to related International Application No. PCT/EP2017/066297, dated Dec. 20, 2017; 14 pages.

*Primary Examiner* — Dominic J Bologna
(74) *Attorney, Agent, or Firm* — Sterne, Kessler, Goldstein & Fox P.L.L.C.

(57) ABSTRACT

A method and apparatus are described for providing an accurate and robust measurement of a lithographic characteristic or metrology parameter. The method includes providing a range or a plurality of values for each of a plurality of metrology parameters of a metrology target, providing a constraint for each of the plurality of metrology parameters, and calculating, by a processor to optimize/modify these parameters within the range of the plurality of values, resulting in a plurality of metrology target designs having metrology parameters meeting the constraints.

9 Claims, 15 Drawing Sheets

(52) U.S. Cl.
CPC ...... *G03F 7/70633* (2013.01); *G03F 7/70683* (2013.01); *G03F 9/7019* (2013.01)

(56) References Cited

U.S. PATENT DOCUMENTS

| | | |
|---|---|---|
| 2006/0066855 A1 | 3/2006 | Den Boef et al. |
| 2006/0280357 A1 | 12/2006 | Seligson et al. |
| 2010/0201963 A1 | 8/2010 | Cramer et al. |
| 2010/0284008 A1 | 11/2010 | Coene et al. |
| 2011/0027704 A1 | 2/2011 | Cramer et al. |
| 2011/0043791 A1 | 2/2011 | Smilde et al. |
| 2011/0069292 A1 | 3/2011 | Den Boef |
| 2011/0102753 A1 | 5/2011 | Van De Kerkhof et al. |
| 2012/0044470 A1 | 2/2012 | Smilde et al. |
| 2012/0123581 A1 | 5/2012 | Smilde et al. |
| 2013/0035888 A1 | 2/2013 | Kandel et al. |
| 2013/0258310 A1 | 10/2013 | Smilde et al. |
| 2013/0271740 A1 | 10/2013 | Quintanilha |
| 2013/0308142 A1 | 11/2013 | Straaijer |
| 2014/0192338 A1 | 7/2014 | Den Boef |
| 2015/0186582 A1 | 7/2015 | Chen et al. |
| 2016/0140267 A1 | 5/2016 | Chen et al. |
| 2016/0161863 A1 | 6/2016 | Den Boef et al. |
| 2017/0052454 A1 | 2/2017 | Jak et al. |

FOREIGN PATENT DOCUMENTS

| | | | | |
|---|---|---|---|---|
| WO | WO 2015/078669 A1 | 6/2015 | | |
| WO | WO-2015078669 A1 * | 6/2015 | ......... | G03F 7/70633 |
| WO | WO 2015/124391 A1 | 8/2015 | | |
| WO | WO-2015124391 A1 * | 8/2015 | ......... | G03F 7/70633 |
| WO | WO 2016/030255 A2 | 3/2016 | | |
| WO | WO 2016/083076 A1 | 6/2016 | | |

* cited by examiner

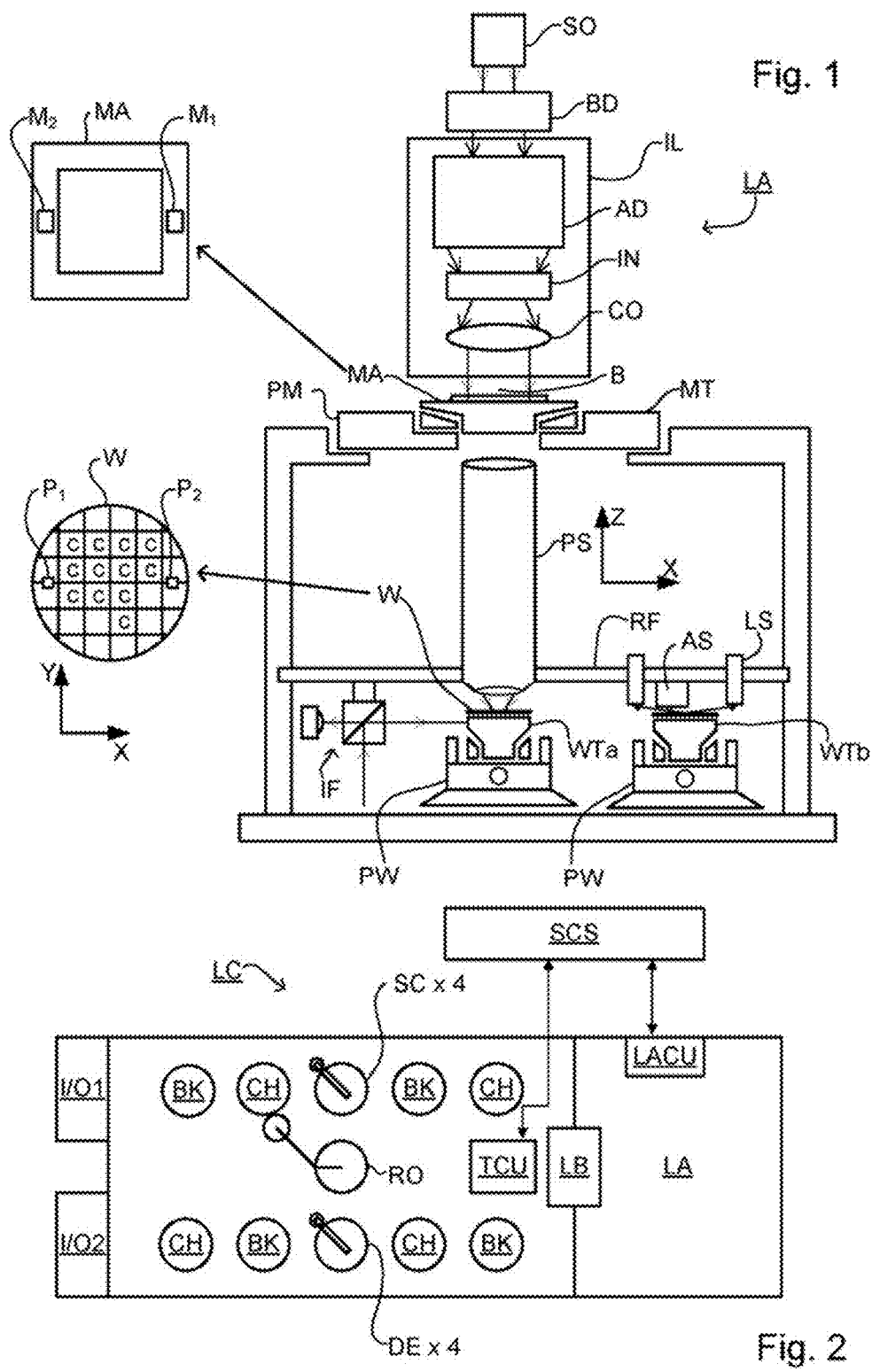

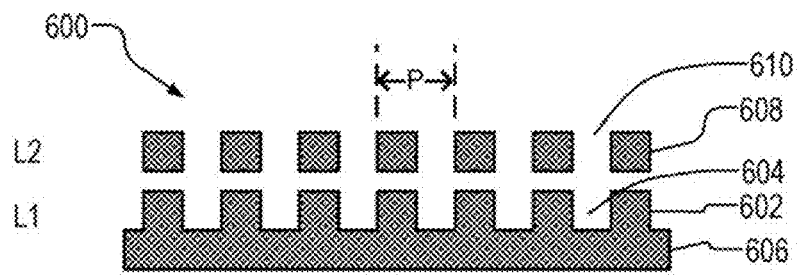
Fig. 7A
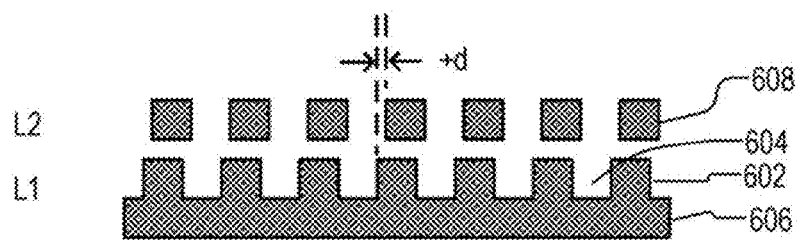
Fig. 7B
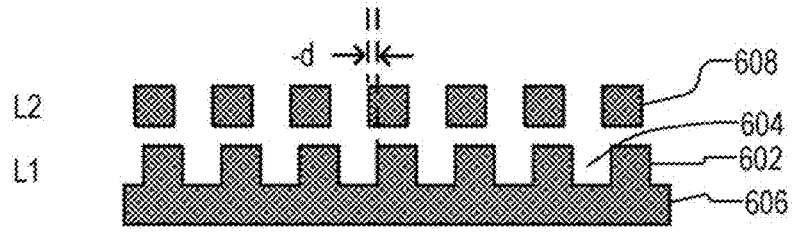
Fig. 7C
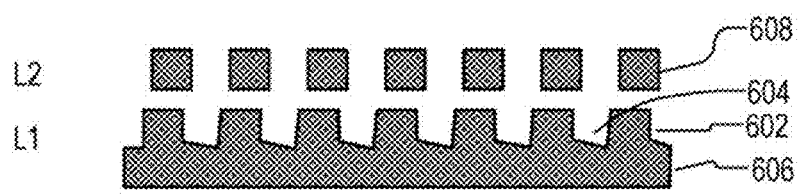
Fig. 7D
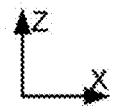

US 10,437,163 B2

METHOD AND APPARATUS FOR DESIGN OF A METROLOGY TARGET

This application incorporates by reference in their entireties U.S. Provisional Patent Application No. 62/362,812, filed Jul. 15, 2016 and U.S. Provisional Application 62/385,615, filed Sep. 9, 2016.

FIELD

The present description relates to methods and apparatus to determine one or more structural parameters of a metrology target usable, for example, in the manufacture of devices by a lithographic technique and to methods of manufacturing using a lithographic technique.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti parallel to this direction. It is also possible to transfer the pattern from the patterning device to the substrate by imprinting the pattern onto the substrate.

In lithographic processes, it is desirable to frequently make measurements of the structures created, e.g., for process control and verification. One or more parameters of the structures are typically measured or determined, for example the overlay error between successive layers formed in or on the substrate. There are various techniques for making measurements of the microscopic structures formed in a lithographic process. Various tools for making such measurements are known, including scanning electron microscopes, which are often used to measure critical dimension (CD), and specialized tools to measure overlay, the accuracy of alignment of two layers in a device. An example of such a tool is a scatterometer developed for use in the lithographic field. This device directs a beam of radiation onto a target on the surface of the substrate and measures one or more properties of the redirected radiation—e.g., intensity at a single angle of reflection as a function of wavelength; intensity at one or more wavelengths as a function of reflected angle; or polarization as a function of reflected angle—to obtain a "spectrum" from which a property of interest of the target can be determined. Determination of the property of interest may be performed by various techniques: e.g., reconstruction of the target structure by iterative approaches such as rigorous coupled wave analysis or finite element methods, library searches, and principal component analysis.

SUMMARY

This invention relates to a method of designing a metrology target and a method of measurement of a lithographic characteristic using a metrology target and a metrology apparatus.

Optical metrology uses light scattered from a target to provide information about a lithographic process. The measurements are performed in optical instruments such as scatterometers. The information that scatterometers are suitable to measure is overlay, which is a relative distance between two overlapping gratings, in a plane parallel with the two overlapping gratings.

In a diffraction based overlay measurement, the overlay is extracted from a difference in the light intensity for the first positive and negative first diffracted order. The stack sensitivity is defined as a ratio of overlay sensitivity K, which is a proportionality factor linking measured light intensity and overlay OV, and averaged light intensity Im, ratio multiplied by 20nm.

Examples of known scatterometers include those scatterometers described in US2006033921A1, US2010201963A1, US2006066855A1, US2014192338, US2011069292A1, US20110027704A, US20110043791A, US2011102753A1, US20120044470A, US20120123581A, US20130258310A, US20130271740A and WO2016083076A1. The contents of all these applications are specifically and entirely incorporated herein by reference.

Further, it is desirable to be able to use a metrology target which his selected such that, when used in a metrology measurement, it provides an optimal and robust result, which in turn leads to accurate overlay measurement. More information about target design is in Appendix, which is specifically and entirely incorporated herein by reference.

One of the problems faced by metrology applications of diffraction based overlay is that the stack sensitivity (one of the parameters of the metrology measurement process, i.e. a metrology parameter) is proportional to the wavelength of the light used when illuminating the target.

Said proportionality of the stack sensitivity with wavelength shows also decreased periodicity as a function of wavelength when the vertical distance (thickness), between the gratings used to form the target, becomes larger.

Furthermore, the process of selecting and/or adjusting the light used in the metrology process is difficult as it puts constraints on the type of source providing the light in illuminating the target and it puts also constraints on the wavelength selecting means used in such metrology apparatus.

It is desirable, for example, to provide methods and apparatus for design of a metrology target. Furthermore, although not limited to this, it would be of advantage if the methods and apparatus could be applied to accurately measure and minimize overlay error in lithographic process.

An object of the current invention is to provide a method of accurate and robust measurement of a lithographic characteristic.

According to the present invention, there is provided a method of metrology target design, the method comprising: receiving an illumination parameter for measuring a metrology target and selecting and/or adjusting a metrology parameter associated with the metrology target design for enhancing an accuracy and/or a robustness of the measurement of the metrology target design using the illumination parameter.

Further, according to the present invention, there is provided a method to determine a parameter of a litho process comprising: receiving the light scattered from a region comprising at least two metrology targets optimized to provide a robust and optimal metrology measurement and determining the parameter of the litho process from a weighted contribution of each individual metrology targets.

The illumination parameter is the wavelength or the polarization of the illuminating beam of the metrology apparatus, for example.

A metrology parameter is, for example, the pitch of the gratings used to form the metrology target. Another metrology parameter is the CD, the angle of the lines forming the gratings, the duty cycle of lines and spaces forming the grating.

In one embodiment of the invention, the pitch of the target is selected and/or adjusted in metrology simulation package, such as Design for Control package, to have large K value of the overlay sensitivity when the target is illuminated with the radiation received from a user or selected in the metrology target design.

In another embodiment of the invention, a cluster of N targets is designed, by selecting and/or adjusting the pitch, CD, angle of the grating forming lines, duty cycle of the line and spaces.

When illuminated with an illumination radiation, which has a wavelength received and used in the design of the metrology target and/or is used as a constraint in the design phase, the cluster of targets will provide at least N overlay sensitivity values, $K_i$.

The simulation package selects and/or adjusts metrology parameters such that the weighted sum of $K_i$ is maxim.

The weighs of each $K_i$ are parameters $\alpha_i$. A further condition for design is that the sum of $\alpha_i=1$ and $-1<\alpha_i<1$.

A parameter of the lithographic process, such as overlay, is determined, for example, as a weighted sum of the overlay values measured from each target wherein the weights are coefficients $\alpha_i$.

In another embodiment of the invention, a cluster of N targets is designed, by selecting and/or adjusting the pitch, CD, angle of the grating forming lines, duty cycle of the line and spaces.

When illuminated with an illumination radiation, which has a wavelength received and used in the design of the metrology target, the cluster of targets will provide at least N overlay numbers, $OV_i$.

The simulation package selects and/or adjusts metrology parameters such that the weighted sum of $OV_i$ is maxim.

The weighs of each Ki are parameters $\alpha_i^{OV}$.

The final overlay number is then a combination, for example linear, of the individual overlay numbers for the different targets.

The reference overlay number, which is the target to approach, is provided by a self-referencing metrology method or it is provided from a CD-SEM measurement.

The weights $\alpha_i^{OV}$ are not bound to interval of values.

The parameters $\alpha_i^{OV}$ are determined, for example, from a correlation analysis. An example of a correlation analysis is PCA (Principal Component Analysis).

A parameter of the lithographic process, such as overlay, is determined, for example, as a weighted sum of the overlay values measured from each target wherein the weights are coefficients $\alpha_i^{OV}$.

In an aspect of the present disclosure, there is provided a range or a plurality of values for each of a plurality of metrology parameters of a metrology target, providing a constraint for each of the plurality of metrology parameters, and calculating, by a processor to optimize these parameters within the range of the plurality of values, resulting in a plurality of metrology target designs having metrology parameters meeting the constraints.

In an aspect of the present disclosure, there is provided a method comprising measuring a modification value and a lithographic process parameter for each metrology target of a plurality of metrology targets, the plurality of metrology targets having been produced by metrology parameters and a manufacturing process. The method further comprises determining a multiplication factor for each metrology target based on its corresponding modification value, and determining an overall lithographic process parameter for the plurality of metrology targets using the modification value and the determined multiplication factors.

In an aspect of the present disclosure, there is provided a method comprising measuring a modification value and a lithographic process parameter for each metrology target of a plurality of metrology targets, the plurality of metrology targets having been produced by metrology parameters and a manufacturing process. The method further comprises determining a multiplication factor for each metrology target based on its corresponding modification value and a reference lithographic process parameter, and determining an overall lithographic process parameter for the plurality of metrology targets using the determined multiplication factors.

BRIEF DESCRIPTION OF THE DRAWINGS

Embodiments will now be described, by way of example only, with reference to the accompanying drawings in which:

FIG. 1 schematically depicts an embodiment of a lithographic apparatus;

FIG. 2 schematically depicts an embodiment of a lithographic cell or cluster;

FIG. 7A, FIG. 7B and FIG. 7C respectively show schematic cross-sections of overlay periodic structures having different overlay values in the region of zero;

FIG. 7D is a schematic cross-section of an overlay periodic structure having structural asymmetry in a bottom periodic structure due to processing effects;

DETAILED DESCRIPTION

Figure 3:
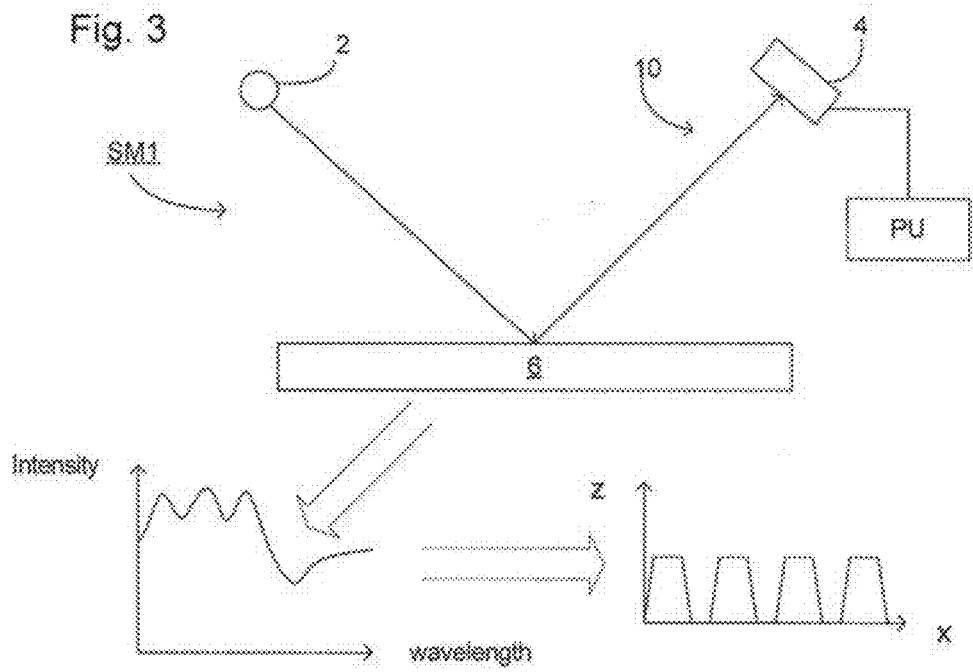
FIG. 3 schematically depicts an embodiment of a scatterometer.

Before describing embodiments in detail, it is instructive to present an example environment in which embodiments may be implemented.

FIG. 1 schematically depicts a lithographic apparatus LA. The apparatus comprises:

an illumination system (illuminator) IL configured to condition a radiation beam B (e.g. DUV radiation or EUV radiation);

a support structure (e.g. a mask table) MT constructed to support a patterning device (e.g. a mask) MA and connected to a first positioner PM configured to accurately position the patterning device in accordance with certain parameters;

a substrate table (e.g. a wafer table) WTa constructed to hold a substrate (e.g. a resist-coated wafer) W and connected to a second positioner PW configured to accurately position the substrate in accordance with certain parameters; and a projection system (e.g. a refractive projection lens system) PS configured to project a pattern imparted to the radiation beam B by patterning device MA onto a target portion C (e.g. comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The patterning device support structure holds the patterning device in a manner that depends on the orientation of the patterning device, the design of the lithographic apparatus, and other conditions, such as for example whether or not the patterning device is held in a vacuum environment. The patterning device support structure can use mechanical, vacuum, electrostatic or other clamping techniques to hold the patterning device. The patterning device support structure may be a frame or a table, for example, which may be fixed or movable as required. The patterning device support structure may ensure that the patterning device is at a desired position, for example with respect to the projection system. Any use of the terms "reticle" or "mask" herein may be considered synonymous with the more general term "patterning device".

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (dual stage) or more tables (e.g., two or more substrate table, two or more patterning device support structures, or a substrate table and metrology table). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may include an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may include various other components, such as an integrator IN and a condenser CO. The illuminator may be used to condition the radiation beam, to have a desired uniformity and intensity distribution in its cross section.

The radiation beam B is incident on the patterning device (e.g., mask) MA, which is held on the patterning device support (e.g., mask table MT), and is patterned by the patterning device. Having traversed the patterning device (e.g., mask) MA, the radiation beam B passes through the projection system PS, which focuses the beam onto a target portion C of the substrate W. With the aid of the second positioner PW and position sensor IF (e.g., an interferometric device, linear encoder, 2-D encoder or capacitive sensor), the substrate table WTa can be moved accurately, e.g., so as to position different target portions C in the path of the radiation beam B. Similarly, the first positioner PM and another position sensor (which is not explicitly depicted in FIG. 1) can be used to accurately position the patterning device (e.g., mask) MA with respect to the path of the radiation beam B, e.g., after mechanical retrieval from a mask library, or during a scan. In general, movement of the patterning device support (e.g., mask table) MT may be realized with the aid of a long-stroke module (coarse positioning) and a short-stroke module (fine positioning), which form part of the first positioner PM. Similarly, movement of the substrate table WTa may be realized using a long-stroke module and a short-stroke module, which form part of the second positioner PW. In the case of a stepper (as opposed to a scanner) the patterning device support (e.g., mask table) MT may be connected to a short-stroke actuator only, or may be fixed.

Patterning device (e.g., mask) MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device (e.g., mask) MA, the mask alignment marks may be located between the dies. Small alignment markers may also be included within dies, in amongst the device features, in which case it is desirable that the markers be as small as possible and not require any different imaging or process conditions than adjacent features. The alignment system, which detects the alignment markers is described further below.

The depicted apparatus could be used in at least one of the following modes:

1. In step mode, the patterning device support (e.g., mask table) MT and the substrate table WTa are kept essentially stationary, while an entire pattern imparted to the radiation beam is projected onto a target portion C at one time (i.e., a single static exposure). The substrate table WTa is then shifted in the X and/or Y direction so that a different target portion C can be exposed. In step mode, the maximum size of the exposure field limits the size of the target portion C imaged in a single static exposure.

2. In scan mode, the patterning device support (e.g., mask table) MT and the substrate table WTa are scanned synchronously while a pattern imparted to the radiation beam is projected onto a target portion C (i.e., a single dynamic exposure). The velocity and direction of the substrate table WTa relative to the patterning device support (e.g., mask table) MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the patterning device support (e.g., mask table) MT is kept essentially stationary holding a programmable patterning device, and the substrate table WTa is moved or scanned while a pattern imparted to the radiation beam is projected onto a target portion C. In this mode, generally a pulsed radiation source is employed and the programmable patterning device is updated as required after each movement of the substrate table WTa or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Lithographic apparatus LA is of a so-called dual stage type which has two tables WTa, WTb (e.g., two substrate tables) and two stations—an exposure station and a measurement station—between which the tables can be exchanged. For example, while a substrate on one table is being exposed at the exposure station, another substrate can be loaded onto the other substrate table at the measurement station and various preparatory steps carried out. The preparatory steps may include mapping the surface control of the substrate using a level sensor LS and measuring the position of alignment markers on the substrate using an alignment sensor AS, both sensors being supported by a reference frame RF. If the position sensor IF is not capable of measuring the position of a table while it is at the measurement station as well as at the exposure station, a second position sensor may be provided to enable the positions of the table to be tracked at both stations. As another example, while a substrate on one table is being exposed at the exposure station, another table without a substrate waits at the measurement station (where optionally measurement activity may occur). This other table has one or more measurement devices and may optionally have other tools (e.g., cleaning apparatus). When the substrate has completed exposure, the table without a substrate moves to the exposure station to perform, e.g., measurements and the table with the substrate moves to a location (e.g., the measurement station) where the substrate is unloaded and another substrate is load. These multi-table arrangements enable a substantial increase in the throughput of the apparatus.

As shown in FIG. 2, the lithographic apparatus LA forms part of a lithographic cell LC, also sometimes referred to as a lithocell or lithocluster, which also includes apparatus to perform one or more pre- and post-exposure processes on a substrate. Conventionally these include one or more spin coaters SC to deposit a resist layer, one or more developers DE to develop exposed resist, one or more chill plates CH and one or more bake plates BK. A substrate handler, or robot, RO picks up a substrate from input/output ports I/O1, 1/O2, moves it between the different process devices and delivers it to the loading bay LB of the lithographic apparatus. These devices, which are often collectively referred to as the track, are under the control of a track control unit TCU which is itself controlled by the supervisory control system SCS, which also controls the lithographic apparatus via lithographic control unit LACU. Thus, the different apparatus may be operated to maximize throughput and processing efficiency.

FIG. 3 depicts an embodiment of a scatterometer SM1. It comprises a broadband (white light) radiation projector 2 which projects radiation onto a substrate 6. The reflected radiation is passed to a spectrometer detector 4, which measures a spectrum 10 (i.e. a measurement of intensity as a function of wavelength) of the specular reflected radiation. From this data, the structure or profile giving rise to the detected spectrum may be reconstructed by processing unit PU, e.g. by Rigorous Coupled Wave Analysis and non-linear regression or by comparison with a library of simulated spectra as shown at the bottom of FIG. 3. In general, for the reconstruction, the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer.

Figure 4:
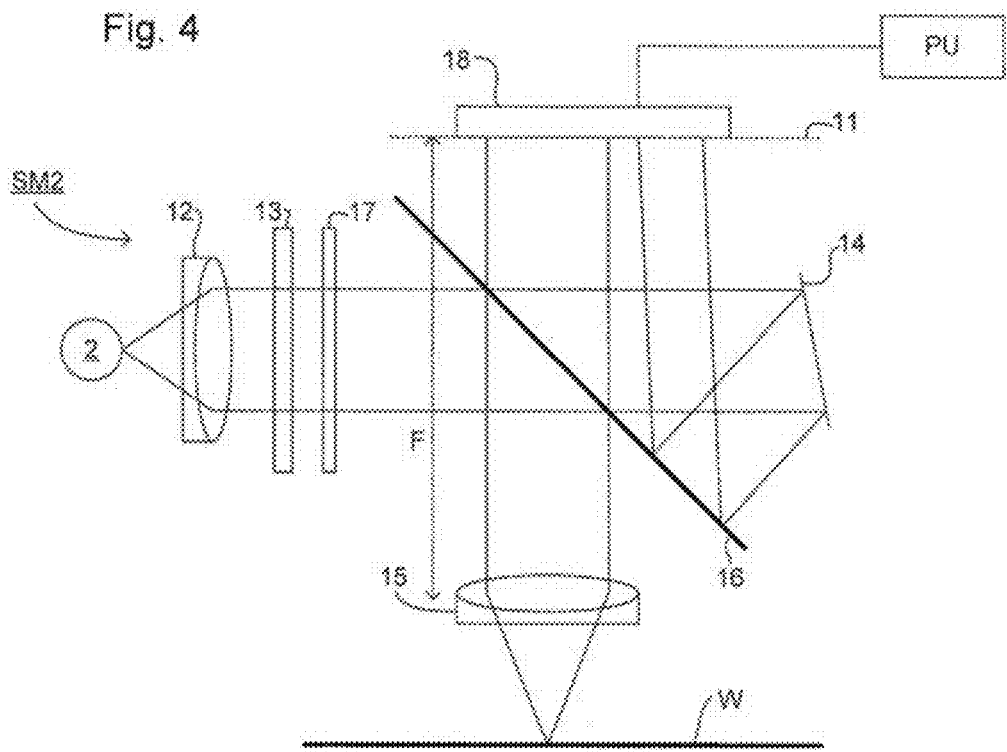
FIG. 4 schematically depicts a further embodiment of a scatterometer.

Another embodiment of a scatterometer SM2 is shown in FIG. 4. In this device, the radiation emitted by radiation source 2 is focused using lens system 12 through interference filter 13 and polarizer 17, reflected by partially reflective surface 16 and is focused onto substrate W via a microscope objective lens 15, which has a high numerical aperture (NA), desirably at least 0.9 or at least 0.95. An immersion scatterometer may even have a lens with a numerical aperture over 1. The reflected radiation then transmits through partially reflective surface 16 into a detector 18 in order to have the scatter spectrum detected. The detector may be located in the back-projected pupil plane 11, which is at the focal length of the lens 15, however the pupil plane may instead be re-imaged with auxiliary optics (not shown) onto the detector 18. The pupil plane is the plane in which the radial position of radiation defines the angle of incidence and the angular position defines the azimuth angle of the radiation. The detector is desirably a two-dimensional detector so that a two-dimensional angular scatter spectrum (i.e. a measurement of intensity as a function of angle of scatter) of the substrate target can be measured. The detector 18 may be, for example, an array of CCD or CMOS sensors, and may have an integration time of, for example, 40 milliseconds per frame.

A reference beam is often used, for example, to measure the intensity of the incident radiation. To do this, when the radiation beam is incident on the partially reflective surface 16 part of it is transmitted through the surface as a reference beam towards a reference mirror 14. The reference beam is then projected onto a different part of the same detector 18.

One or more interference filters 13 are available to select a wavelength of interest in the range of, say, 405-790 nm or even lower, such as 200-300 nm. The interference filter(s) may be tunable rather than comprising a set of different filters. A grating could be used instead of or in addition to one or more interference filters.

The detector 18 may measure the intensity of scattered radiation at a single wavelength (or narrow wavelength range), the intensity separately at multiple wavelengths or the intensity integrated over a wavelength range. Further, the detector may separately measure the intensity of transverse magnetic—(TM) and transverse electric—(TE) polarized radiation and/or the phase difference between the transverse magnetic- and transverse electric-polarized radiation.

Using a broadband radiation source 2 (i.e. one with a wide range of radiation frequencies or wavelengths—and therefore of colors) is possible, which gives a large etendue, allowing the mixing of multiple wavelengths. The plurality of wavelengths in the broadband desirably each has a bandwidth of $\delta\lambda$ and a spacing of at least $2\delta\lambda$ (i.e. twice the wavelength bandwidth). Several "sources" of radiation may be different portions of an extended radiation source which have been split using, e.g., fiber bundles. In this way, angle resolved scatter spectra may be measured at multiple wavelengths in parallel. A 3-D spectrum (wavelength and two different angles) may be measured, which contains more information than a 2-D spectrum. This allows more information to be measured which increases metrology process robustness. This is described in more detail in U.S. patent application publication no. US 2006-0066855, which document is hereby incorporated in its entirety by reference.

By comparing one or more properties of the beam before and after it has been redirected by the target, one or more properties of the substrate may be determined. This may be done, for example, by comparing the redirected beam with theoretical redirected beams calculated using a model of the substrate and searching for the model that gives the best fit between measured and calculated redirected beams. Typically a parameterized generic model is used and the parameters of the model, for example width, height and sidewall angle of the pattern, are varied until the best match is obtained.

Two main types of scatterometers are used. A spectroscopic scatterometer directs a broadband radiation beam onto the substrate and measures the spectrum (intensity as a function of wavelength) of the radiation scattered into a particular narrow angular range. An angularly resolved scatterometer uses a monochromatic radiation beam and measures the intensity (or intensity ratio and phase difference in case of an ellipsometric configuration) of the scattered radiation as a function of angle. Alternatively, measurement signals of different wavelengths may be measured separately and combined at an analysis stage. Polarized radiation may be used to generate more than one spectrum from the same substrate.

In order to determine one or more parameters of the substrate, a best match is typically found between the theoretical spectrum produced from a model of the substrate and the measured spectrum produced by the redirected beam as a function of either wavelength (spectroscopic scatterometer) or angle (angularly resolved scatterometer). To find the best match there are various methods, which may be combined. For example, a first method is an iterative search method, where a first set of model parameters is used to calculate a first spectrum, a comparison being made with the measured spectrum. Then a second set of model parameters is selected, a second spectrum is calculated and a comparison of the second spectrum is made with the measured spectrum. These steps are repeated with the goal of finding the set of parameters that gives the best matching spectrum. Typically, the information from the comparison is used to steer the selection of the subsequent set of parameters. This process is known as an iterative search technique. The model with the set of parameters that gives the best match is considered to be the best description of the measured substrate.

A second method is to make a library of spectra, each spectrum corresponding to a specific set of model parameters. Typically the sets of model parameters are chosen to cover all or almost all possible variations of substrate properties. The measured spectrum is compared to the spectra in the library. Similarly to the iterative search method, the model with the set of parameters corresponding to the spectrum that gives the best match is considered to be the best description of the measured substrate. Interpolation techniques may be used to determine more accurately the best set of parameters in this library search technique.

In any method, sufficient data points (wavelengths and/or angles) in the calculated spectrum should be used in order to enable an accurate match, typically between 80 up to 800 data points or more for each spectrum. Using an iterative method, each iteration for each parameter value would involve calculation at 80 or more data points. This is multiplied by the number of iterations needed to obtain the correct profile parameters. Thus many calculations may be required. In practice this leads to a compromise between accuracy and speed of processing. In the library approach, there is a similar compromise between accuracy and the time required to set up the library.

In any of the scatterometers described above, the target on substrate W may be a grating which is printed such that after development, the bars are formed of solid resist lines. The bars may alternatively be etched into the substrate. The target pattern is chosen to be sensitive to a parameter of interest, such as focus, dose, overlay, chromatic aberration in the lithographic projection apparatus, etc., such that variation in the relevant parameter will manifest as variation in the printed target. For example, the target pattern may be sensitive to chromatic aberration in the lithographic projection apparatus, particularly the projection system PL, and illumination symmetry and the presence of such aberration will manifest itself in a variation in the printed target pattern. Accordingly, the scatterometry data of the printed target pattern is used to reconstruct the target pattern. The parameters of the target pattern, such as line width and shape, may be input to the reconstruction process, performed by a processing unit PU, from knowledge of the printing step and/or other scatterometry processes.

While embodiments of a scatterometer have been described herein, other types of metrology apparatus may be used in an embodiment. For example, a dark field metrology apparatus such as described in U.S. Patent Application Publication No. 2013-0308142, which is incorporated herein in its entirety by reference, may be used. Further, those other types of metrology apparatus may use a completely different technique than scatterometry.

Figure 5:
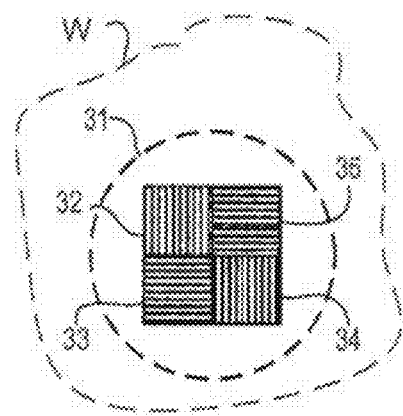
FIG. 5 schematically depicts a form of multiple grating target and an outline of a measurement spot on a substrate.

FIG. 5 depicts an example composite metrology target formed on a substrate according to known practice. The composite target comprises four gratings 32, 33, 34, 35 positioned closely together so that they will all be within a measurement spot 31 formed by the illumination beam of the metrology apparatus. The four targets thus are all simultaneously illuminated and simultaneously imaged on sensor 4, 18. In an example dedicated to overlay measurement, gratings 32, 33, 34, 35 are themselves composite gratings formed by overlying gratings that are patterned in different layers of the semi-conductor device formed on substrate W. There may be a plurality of composite targets placed at different locations on substrate W such that measurements and information about the entire substrate W can be obtained. Gratings 32, 33, 34, 35 may have differently biased overlay offsets in order to facilitate measurement of overlay between the layers in which the different parts of the composite gratings are formed. Gratings 32, 33, 34, 35 may also differ in their orientation, as shown, so as to diffract incoming radiation in X and Y directions. In one example, gratings 32 and 34 are X-direction gratings with biases of +d, −d, respectively. This means that grating 32 has its overlying components arranged so that if they were both printed exactly at their nominal locations, one of the components would be offset relative to the other by a distance d. Grating 34 has its components arranged so that if perfectly printed there would be an offset of d, but in the opposite direction to the first grating and so on. Gratings 33 and 35 may be Y-direction gratings with offsets +d and −d respectively. While four gratings are illustrated, another embodiment may include a larger matrix to obtain desired accuracy. For example, a 3×3 array of nine composite gratings may have biases −4d, −3d, −2d, −d, 0, +d, +2d, +3d, +4d. Separate images of these gratings can be identified in the image captured by sensor 4, 18.

The metrology targets as described herein may be, for example, overlay targets designed for use with a metrology tool such as Yieldstar stand-alone or integrated metrology tool, and/or alignment targets such as those typically used with a TwinScan lithographic system, both available from ASML.

In general, metrology targets for use with such systems should be printed on the substrate with dimensions that meet the design specification for the particular microelectronic device to be imaged on that substrate. As processes continue to push against the limits of lithographic device imaging resolution in advanced process nodes, the design rule and process compatibility requirements place stress on the selection of appropriate targets. As the targets themselves become more advanced, often requiring the use of resolution enhancement technology, such as phase-shift patterning devices, and optical proximity correction, the printability of the target within the process design rules becomes less certain. As a result, proposed metrology target design may be subject to testing and/or simulation in order to confirm their suitability and/or viability, both from a printability and a detectability standpoint. In a commercial environment, good overlay mark detectability may be considered to be a combination of low total measurement uncertainty as well as a short move-acquire-move time, as slow acquisition is detrimental to total throughput for the production line. Modern micro-diffraction-based-overlay targets (µDBO) may be on the order of 10 µm on a side, which provides an inherently low detection signal compared to 40×160 µm2 targets such as those used in the context of monitor substrates.

Additionally, once metrology targets that meet the above criteria have been selected, there is a possibility that detectability will change with respect to process variations, such as film thickness variation, various etch biases, and geometry asymmetries induced by the etch and/or polish processes. Therefore, it may be useful to select a target that has low detectability variation and low overlay/alignment variation against various process variations. Likewise, the fingerprint (printing characteristics, including, for example, lens aberration) of the specific machine that is to be used to produce the microelectronic device to be imaged will, in general, affect the imaging and production of the metrology targets. It may therefore be useful to ensure that the metrology targets are resistant to fingerprint effects, as some patterns will be more or less affected by a particular lithographic fingerprint.

Figures 6A, 6B:
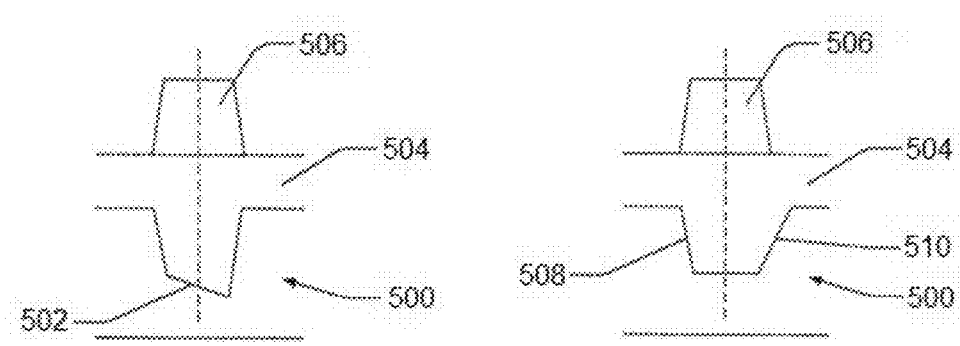
FIGS. 6A and 6B schematically depict a model structure of one period of an overlay target showing an example of variation of the target from ideal, e.g., two types of process-induced asymmetry.

FIGS. 6A and 6B schematically show a model structure of one period of an overlay target showing an example of variation of the target from ideal, e.g., two types of process-induced asymmetry. With reference to FIG. 6A, the substrate W is patterned with a bottom grating 500, etched into a substrate layer. The etch process used for the bottom grating results in a tilt of the floor 502 of the etched trench. This floor tilt, FT, can be represented as a structural parameter, for example as a measure of the height drop across the floor 502, in nm. A BARC (bottom anti-reflective coating) layer 504 supports the patterned resist feature of the top grating 506. In this example, the alignment overlay error between the top and bottom grating is zero, as the centers of the top and bottom grating features are at the same lateral position. However, the bottom-layer process-induced asymmetry, i.e. the floor tilt, leads to an error in the measured overlay offset, in this case giving a non-zero overlay offset. FIG. 6B shows another type of bottom-layer process-induced asymmetry that can lead to an error in the measured overlay offset. This is side wall angle (SWA) unbalance, SWAun. Features in common with those of FIG. 6A are labeled the same. Here, one side wall 508 of the bottom grating has a different slope to the other side wall 510. This unbalance can be represented as a structural parameter, for example as a ratio of the two side wall angles relative to the plane of the substrate. Both asymmetry parameters floor tilt and SWA unbalance give rise to an "apparent" overlay error between the top and bottom gratings. This apparent overlay error comes on top of the "real" overlay error to be measured between the top and bottom gratings.

Accordingly, in an embodiment, it is desirable to simulate various metrology target designs in order to confirm the suitability and/or viability of one or more of the proposed target designs.

In the patent application publications mentioned above, various techniques are disclosed for improving the quality of overlay measurements using the basic method mentioned above. These techniques will not be explained here in further detail. They may be used in combination with the techniques newly disclosed in the present application.

FIGS. 7A-7D show schematic cross-sections of target periodic structures (overlay periodic structures), with different bias offsets. These can be used as the target T on substrate W. Periodic structures with periodicity in the X direction are shown for the sake of example only. Different combinations of these periodic structures with different biases and with different orientations can be provided separately or as part of a target. Further details of the design of these periodic target structures are described in U.S. Patent Publication US 20150186582, which is hereby incorporated by reference in its entirety.

Starting with FIG. 7A, a target 600 formed in at least two layers, labeled L1 and L2, is shown. In the lower or bottom layer L1, a first periodic structure (the lower or bottom periodic structure), for example a grating, is formed by features 602 and spaces 604 on a substrate 606. In layer L2, a second periodic structure, for example a grating, is formed by features 608 and spaces 610. (The cross-section is drawn such that the features 602, 608 (e.g., lines) extend into the page.) The periodic structure pattern repeats with a pitch P in both layers. Features 602 and 608 may take the form of lines, dots, blocks and via holes. In the situation shown at FIG. 7A, there is no overlay contribution due to misalignment, e.g., no overlay error and no imposed bias, so that each feature 608 of the second structure lies exactly over a feature 602 in the first structure.

At FIG. 7B, the same target with a first known imposed bias +d is shown, such that the features 608 of the first structure are shifted by a distance d to the right, relative to the features of the second structure. The bias distance d might be a few nanometers in practice, for example 10 nm-20 nm, while the pitch P is for example in the range 300-1000 nm, for example 500 nm or 600 nm. At FIG. 7C, another feature with a second known imposed bias −d, such that the features of 608 are shifted to the left, is depicted. The value of d need not be the same for each structure. Biased periodic structures of this type shown at FIGS. 7A to 7C are described in the prior patent application publications mentioned above.

FIG. 7D shows schematically a phenomenon of structural asymmetry, in this case structural asymmetry in the first structure (bottom structure asymmetry). The features in the periodic structures at FIGS. 7A to 7C, are shown as perfectly square-sided, when a real feature would have some slope on the side, and a certain roughness. Nevertheless they are intended to be at least symmetrical in profile. The features 602 and/or spaces 604 at FIG. 7D in the first structure no longer have a symmetrical form at all, but rather have become distorted by one or more processing steps. Thus, for example, a bottom surface of each space has become tilted (bottom wall tilt). For example, side wall angles of the features and spaces have become asymmetrical. As a result of this, the overall target asymmetry of a target will comprise an overlay contribution independent of structural asymmetry (i.e., an overlay contribution due to misalignment of the first structure and second structure; itself comprised of overlay error and any known imposed bias) and a structural contribution due to this structural asymmetry in the target.

When overlay is measured by the method of FIG. 6 using only two biased periodic structures, the process-induced structural asymmetry cannot be distinguished from the overlay contribution due to misalignment, and overlay measurements (in particular to measure the undesired overlay error) become unreliable as a result. Structural asymmetry in the first structure (bottom periodic structure) of a target is a common form of structural asymmetry. It may originate, for example, in the substrate processing steps such as chemical-mechanical polishing (CMP), performed after the first structure was originally formed.

In PCT patent application publication no. WO 2013-143814, it is proposed to use three or more component periodic structures to measure overlay by a modified version of the method of FIG. 6. Three or more periodic structures of the type shown in FIGS. 7A to 7C are used to obtain overlay measurements that are to some extent corrected for structural asymmetry in the target periodic structures, such as is caused by bottom structure asymmetry in a practical patterning process. However, this method requires a new target design (e.g. different to that illustrated in FIG. 4) and therefore a new patterning device or patterning device pattern will be required. Furthermore, the target area is larger and therefore consumes more substrate area. In addition, the phase element of the overlay contribution resultant from structural asymmetry is ignored in this and other prior methods, meaning that the corrections are not as accurate as they could be if the phase element was also corrected for.

Figure 8:
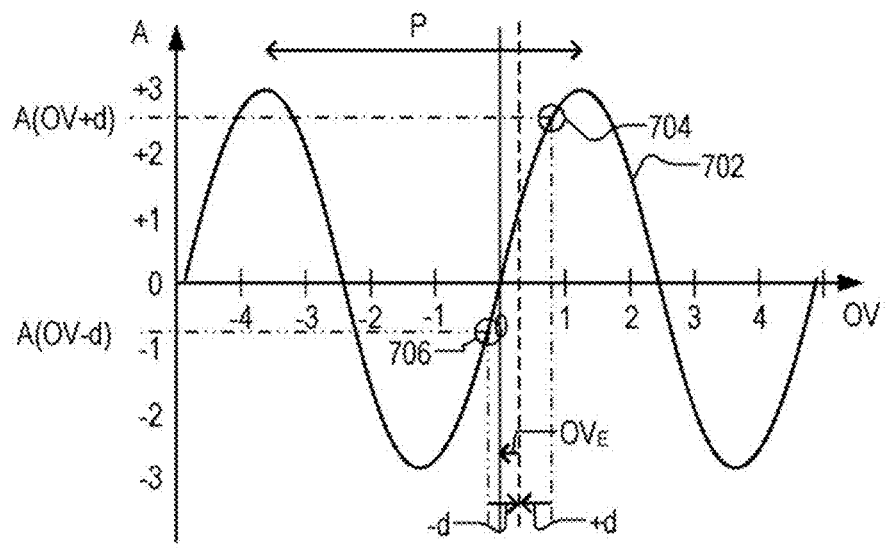
FIG. 8 illustrates principles of overlay measurement in an ideal target, not subject to structural asymmetry.
Figure 9:
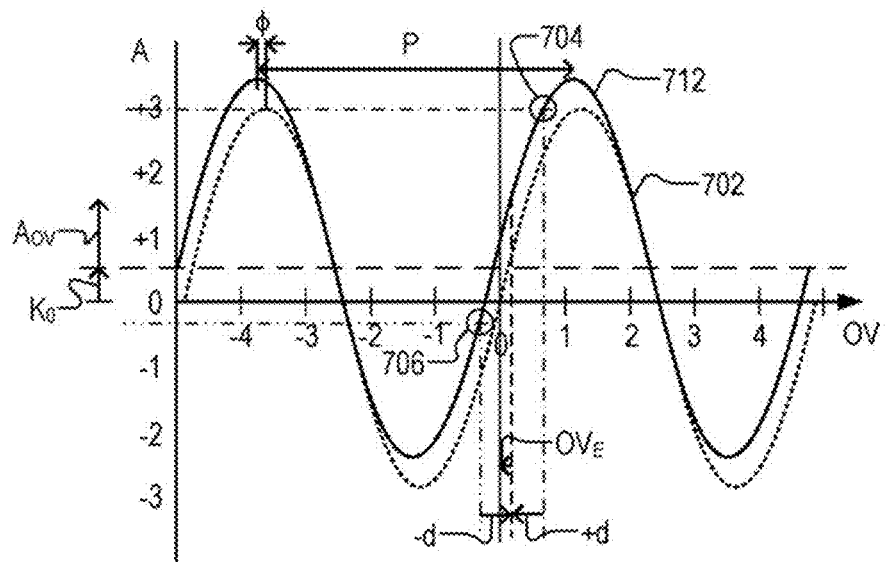
FIG. 9 illustrates principles of overlay measurement in a non-ideal target, with correction of structural asymmetry as disclosed in embodiments herein.

In FIG. 8 a curve 702 illustrates the relationship between overlay OV and intensity asymmetry A for an 'ideal' target having zero offset and no structural asymmetry within the individual periodic structures forming the target, and in particular within the individual periodic structure of the first structure. Consequently, the target asymmetry of this ideal target comprises only an overlay contribution due to misalignment of the first structure and second structure resultant from a known imposed bias and overlay error OV. This graph, and the graph of FIG. 9, illustrate the principles behind the disclosure only, and in each graph, the units of intensity asymmetry A and overlay OV are arbitrary. Examples of actual dimensions will be given further below.

In the 'ideal' situation of FIG. 8, the curve 702 indicates that the intensity asymmetry A has a non-linear periodic relationship (e.g., sinusoidal relationship) with the overlay. The period P of the sinusoidal variation corresponds to the period or pitch P of the periodic structures, converted of course to an appropriate scale. The sinusoidal form is pure in this example, but can include harmonics in real circumstances.

As mentioned above, biased periodic structures (having a known imposed overlay bias) can be used to measure overlay, rather than relying on a single measurement. This bias has a known value defined in the patterning device (e.g. a reticle) from which it was made, that serves as an on-substrate calibration of the overlay corresponding to the measured intensity asymmetry. In the drawing, the calculation is illustrated graphically. In steps S1-S5, intensity asymmetry measurements $A_{+d}$ and $A_{-d}$ are obtained for periodic structures having imposed biases +d and −d respectively (as shown in FIG. 7B and FIG. 7C, for example). Fitting these measurements to the sinusoidal curve gives points 04 and 706 as shown. Knowing the biases, the true overlay error OV can be calculated. The pitch P of the sinusoidal curve is known from the design of the target. The vertical scale or amplitude of the curve 702 is not known to start with, but is an unknown factor which can be referred to as a K value. This K value is a measure of the stack sensitivity of the intensity asymmetry measurements to the target. If the determined K value is not accurate then the overlay determined will also be inaccurate. Furthermore, the K value may be target specific and vary across the substrate due to process variation across the substrate. For example K values between each target may vary due to chemical mechanical polishing or stack thickness.

In equation terms, the relationship between overlay error OV, K value, and intensity asymmetry A is assumed to be:

$$A_{\pm d} = K \sin(OV \pm d) \tag{1}$$

where overlay error OV is expressed on a scale such that the target pitch P corresponds to an angle $2\pi$ radians. Using two measurements of gratings with different, known biases (e.g. +d and −d), the overlay error OV can be calculated using:

$$OV = \mathrm{atan}\left(\frac{A_{+d} + A_{-d}}{A_{+d} - A_{-d}} \cdot \tan(d)\right). \tag{2}$$

Figure 10:
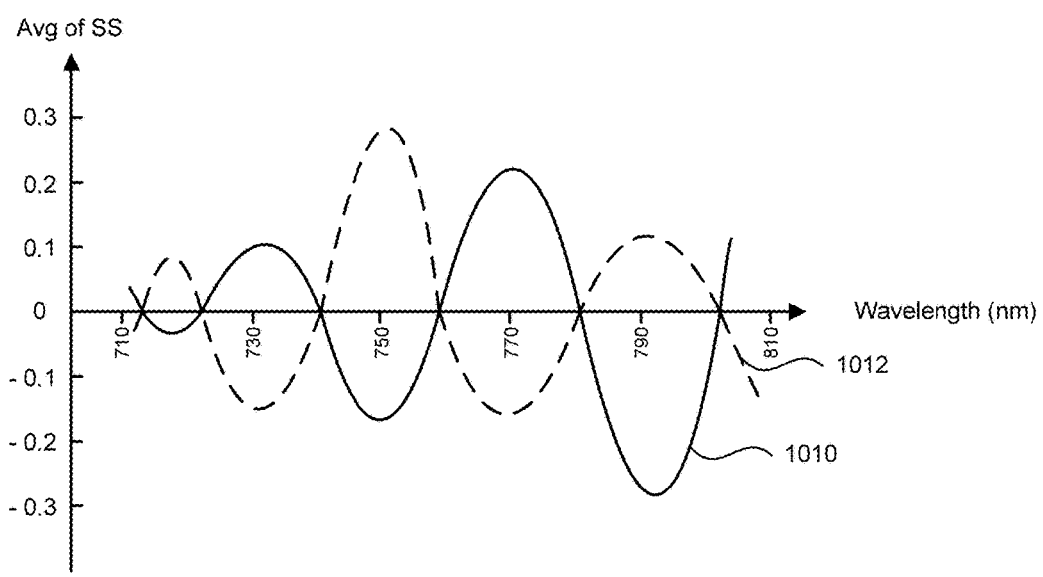
FIG. 10 illustrates an example graph of stack sensitivity as a function of incident radiation wavelength for different incident illumination polarization.

FIG. 10 depicts an example graph of stack sensitivity as a function of incident radiation wavelength. Stack sensitivity can be understood as a measurement of how the sensitivity of intensity asymmetry measurement changes as the incident radiation wavelength is varied. The stack sensitivity or K value varies between different target stacks and is also highly dependent on the wavelength of the incident radiation. Measurements taken at higher K value are more reliable, therefore the stack sensitivity or K value is indicative of target measurability. In the example showed in FIG. 10, a metrology target in the form of a composite grating with, e.g., a 625 nm pitch, is illuminated with incident radiation comprising a spectrum of wavelengths and orthogonal polarizations, and the values of stack sensitivity form swing curves that oscillates between, e.g., 0 and ±0.3 (arbitrary units) as the wavelength changes. Curves 1010 and 1012 are plots of average stack sensitivity with respect to incident radiation wavelength for, e.g., 0 and 90 degrees of orthogonal polarizations, respectively. It should be noted that the stack sensitivity or K values presented here are for exemplary purposes only, and may vary under different radiation conditions or for different targets.

As shown in FIG. 10, it is desirable to select a specific wavelength at which the stack sensitivity reaches a maximum value in order to achieve a more robust and reliable measurement. However, the wavelength selection may have to be accurate in order to meet this condition, and any process variation or change in incident radiation may cause a shift in the swing curves and stack sensitivity may no longer be at its maximum at the previously selected radiation conditions. For example, a variation in stack properties for thick stack devices may lead to shifts in swing curves. The proportionality of stack sensitivity with wavelength shows decreased periodicity as a function of wavelength when the vertical distance between gratings used to form the target becomes larger. This is evident with modern high-density circuitry such as 3D NAND devices, since quite substantial height steps may in fact be present. Stack differences between adjacent periodic structures of a target or between adjacent targets may be a factor that adversely affects the accuracy of measurement, especially overlay measurement. Further details on stack differences and measurement accuracy can be found in European Patent Application EP16166614.4, which is hereby incorporated by reference herein in its entirety.

Stack difference may be understood as an un-designed difference in physical configurations between adjacent periodic structures or targets. Stack difference causes a difference in an optical property (e.g., intensity, polarization, etc.) of measurement radiation between the adjacent periodic structures or targets that is due to other than overlay error, other than intentional bias and other than structural asymmetry common to the adjacent periodic structures or targets. Stack difference includes, but is not limited to, a thickness difference between the adjacent periodic structures or targets (e.g., a difference in thickness of one or more layers such that one periodic structure or target is higher or lower than another periodic structure or target designed to be at a substantially equal level), a refractive index difference between the adjacent periodic structures or targets (e.g., a difference in refractive index of one or more layers such that the combined refractive index for the one or more layers for one periodic structure or target is different than the combined refractive index for the one or more layers for of another periodic structure or target even though designed to have a substantially equal combined refractive index), a difference in material between the adjacent periodic structures or targets (e.g., a difference in the material type, material uniformity, etc. of one or more layers such that there is a difference in material for one periodic structure or target from another periodic structure or target designed to have a substantially same material), a difference in the grating period of the structures of adjacent periodic structures or targets (e.g., a difference in the grating period for one periodic structure or target from another periodic structure or target designed to have a substantially same grating period), a difference in depth of the structures of adjacent periodic structures or targets (e.g., a difference due to etching in the depth of structures of one periodic structure or target from another periodic structure or target designed to have a substantially same depth), a difference in width (CD) of the features of adjacent periodic structures or targets (e.g., a difference in the width of features of one periodic structure or target from another periodic structure or target designed to have a substantially same width of features), etc. In some examples, the stack difference is introduced by processing steps, such as CMP, layer deposition, etching, etc. in the patterning process.

As mentioned above, stack difference causes a change in optical properties of measurement radiation between the adjacent periodic structures or targets, therefore stack sensitivity measurements can be tuned by varying target design parameters, such as grating pitch, CD, or target profiles, as further explained below with reference to FIG. 11.

Figure 11:
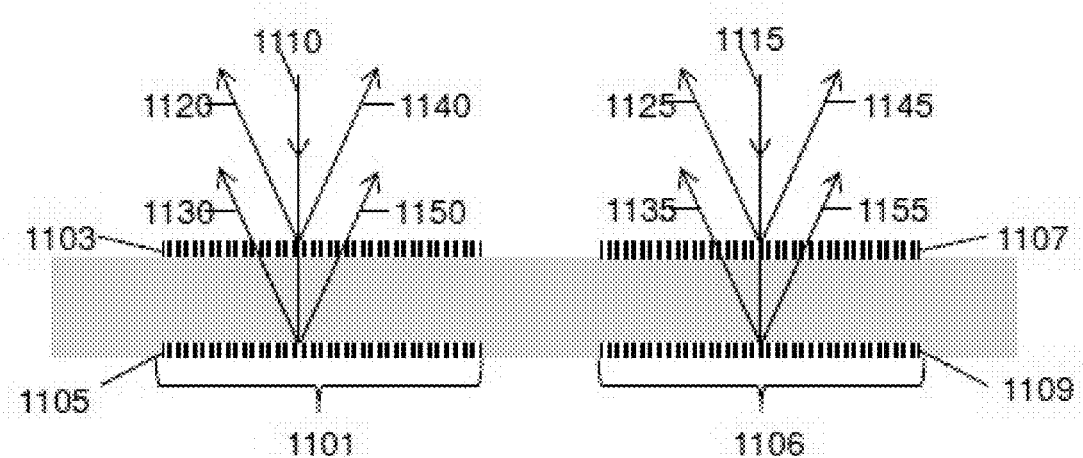
FIG. 11 schematically illustrates a situation where no stack difference exists between a first target periodic structure with a bias +d and a second target periodic structure with a bias −d, and illustrates diffraction signals following diffraction by the first and second target periodic structures.

FIG. 11 shows a first periodic structure 1101 of a target in the form of a composite grating with a bias +d and an adjacent second periodic structure 1106 of the target in the form of a composite grating with a bias −d. A first incident measurement radiation beam 1110 is illuminated on the first structure 1105 and the second structure 1103 of the first periodic structure 1101, where there is a bias +d between the first structure 1105 and the second structure 1103. As a result, −1$^{st}$ diffraction order signals 1130 and 1120 are diffracted by the first structure 1105 and the second structure 1103, respectively. The −1$^{st}$ diffraction order signal diffracted by the first periodic structure 1101, $I'_{-1}{}^{+d}$, may be understood as the combination of the −1$^{st}$ diffraction order signals 1130 and 1120. Additionally, +1$^{st}$ diffraction order signals 1150 and 1140 are diffracted by the first structure 1105 and the second structure 1103, respectively. The +1$^{st}$ diffraction order signal diffracted by the first periodic structure 1101, $I'_{+1}{}^{+d}$, may be understood as the combination of the +1$^{st}$ diffraction order signals 1150 and 1140. Accordingly, the −1$^{st}$ diffraction order signal diffracted by the first periodic structure 1101, $I'_{-1}{}^{+d}$, and the +1$^{st}$ diffraction order signal diffracted by the first periodic structure 1101, $I'_{+1}{}^{+d}$, may be collectively expressed by:

$$I'_{\pm 1}{}^{+d} = 1 + C^* \cos(\beta \pm \varphi_+) \quad (3)$$

where C indicates the contrast of the signal (which is a function of the periodic structure design, measurement wavelength, etc.), $$\beta = 4\pi \frac{T}{\lambda},$$

T is the thickness of the first periodic structure, λ is the measurement radiation wavelength, phase term $$\varphi_+ = 2\pi \frac{OV + d}{P},$$

Figures 12, 13:
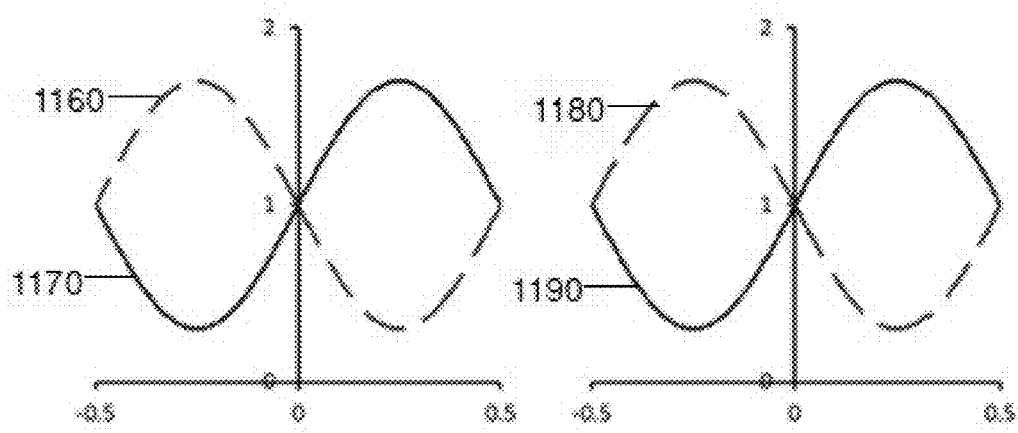
FIG. 12 schematically illustrates the intensity variations of the combined +1st diffraction order signal and the combined −1st diffraction order signal diffracted by the first target periodic structure.
FIG. 13 schematically illustrates the intensity variations of the combined +1st diffraction order signal and the combined −1st diffraction order signal diffracted by the second target periodic structure.

OV is the actual overlay (due to any unintentional misalignment of the layers), and P is the pitch of the first structure 1105 and the second structure 1103 of the first periodic structure 1101. In FIG. 12, the intensity profiles of the −1$^{st}$ diffraction order signal diffracted by the first periodic structure 1101, $I'_{-1}{}^{+d}$ and the +1$^{st}$ diffraction order signal diffracted by the first periodic structure 1101, $I'_{+1}{}^{+d}$ are depicted in traces 1160 and 1170, respectively according to equation (3).

Similarly, a second incident measurement radiation beam 1115 is illuminated on the first structure 1109 and the second structure 1107 of the second periodic structure 1106, where there is a bias −d between the first structure 1109 and the second structure 1106. As a result, −1$^{st}$ diffraction order signals 1135 and 1125 are diffracted by the first structure 1109 and the second structure 1107 of the second periodic structure 1106, respectively. The −1$^{st}$ diffraction order signal diffracted by the second periodic structure 1106, $I'_{-1}{}^{-d}$, may be understood as the combination of the −1$^{st}$ diffraction order signals 1135 and 1125. Additionally, +1$^{st}$ diffraction order signals 1155 and 1145 are diffracted by the first structure 1109 and the second structure 1107, respectively. The +1$^{st}$ diffraction order signal diffracted by the second periodic structure 1106, $I'_{+1}{}^{-d}$, may be understood as the combination of the +1$^{st}$ diffraction order signals 1155 and 1145. Accordingly, the −1$^{st}$ diffraction order signal diffracted by the second periodic structure 1106, $I'_{-1}{}^{-d}$, and the +1$^{st}$ diffraction order signal diffracted by the second periodic structure 1106, $I'_{+1}{}^{-d}$, may be collectively expressed by:

$$I'_{\pm 1}{}^{-d} = 1 + C^* \cos(\beta \pm \varphi_-) \quad (4)$$

where C indicates the contrast of the respective signal, $$\beta = 4\pi \frac{T}{\lambda}, T$$

is the thickness of the second periodic structure, λ is the measurement radiation wavelength, phase term $$\varphi_- = 2\pi \frac{OV - d}{P},$$

OV is the actual overlay (due to any unintentional misalignment of the layers), and P is the pitch of the first structure 1109 and the second structure 1107 of the second periodic structure 1106. In FIG. 13, the intensity profiles of the −1$^{st}$ diffraction order signal diffracted by the second periodic structure 1106, $I'_{-1}{}^{-d}$, and the +1$^{st}$ diffraction order signal diffracted by the second periodic structure 1106, $I'_{+1}{}^{-d}$, are depicted in traces 1180 and 1190, respectively according to equation (4).

Figure 14:
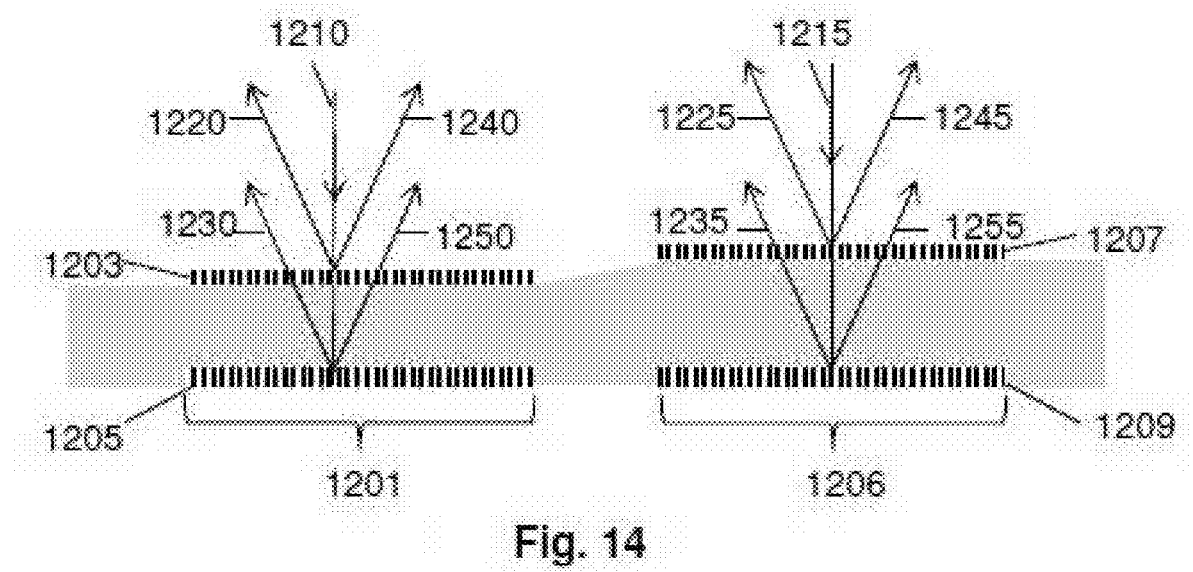
FIG. 14 schematically illustrates a situation where a stack difference exists between a first target periodic structure with a bias +d and a second target periodic structure with a bias −d, and illustrates diffraction signals following diffraction by the first and second target periodic structures.

Now, FIG. 14 illustrates a situation where a stack difference exists between a first periodic structure 1201 with a bias +d and an adjacent second periodic structure 1206 with a bias −d. In this case, the stack difference is a different in thickness as shown in FIG. 14 and described hereafter. Similar to FIG. 13, a first incident measurement radiation beam 1210 is illuminated on the first structure 1205 of the first periodic structure 1201 and the second structure 1203 of the first periodic structure 1201, respectively. As a result, −1$^{st}$ diffraction order signals 1230 and 1220 are diffracted by the first structure 1205 and the second structure 1203, respectively. Accordingly, the −1$^{st}$ diffraction order signal diffracted by the first periodic structure 1201, $I_{+1}^{-d}$, may be understood as the combination of the −1$^{st}$ diffraction order signals 1230 and 1220. Additionally, +1$^{st}$ diffraction order signals 1250 and 1240 are diffracted by the first structure 1205 and the second structure 1203, respectively. Accordingly, the +1$^{st}$ diffraction order signal diffracted by the first periodic structure 1201, $I_{+1}^{-d}$, may be understood as the combination of the +1$^{st}$ diffraction order signals 1250 and 1240.

Similarly, a second incident measurement radiation beam 1215 is illuminated on the first structure 1209 and the second structure 1207 of the second periodic structure 1206, respectively. As a result, −1$^{st}$ diffraction order signals 1235 and 1225 are diffracted by the first structure 1209 and the second structure 1207, respectively. Accordingly, the −1$^{st}$ diffraction order signal diffracted by the second periodic structure 1206, $I_{-1}^{+d}$, may be understood as the combination of the −1$^{st}$ diffraction order signals 1225 and 1235. Additionally, +1$^{st}$ diffraction order signals 1255 and 1245 are diffracted by the first structure 1209 and the second structure 1207, respectively. Accordingly, the +1$^{st}$ diffraction order signal diffracted by the second periodic structure 1206, $I_{+1}^{+d}$, may be understood as the combination of the +1$^{st}$ diffraction order signals 1255 and 1245.

As an example of stack difference, the first periodic structure 1201 and the second periodic structure 1206 may have a difference in thickness as shown in FIG. 14. However, in another example, the stack difference may be created by one or more other factors that allow for an additional or alternative difference in un-designed physical configuration between the first periodic structure 1201 and the second periodic structure 1206. For example, a stack difference may be created when the first periodic structure 1201 is more opaque to the first measurement radiation beam 1210 than the second periodic structure 1206. For example, there may be a difference in material (e.g., a same type of material having a different refractive index, a different type of material, etc.) between the first periodic structure 1201 and the second periodic structure 1206. As another example, there may be a difference in pitch of the first periodic structure 1201 relative to the second periodic structure 1206 even though they are designed to have substantially the same pitch. These examples of stack difference are not the only ways there can be a stack difference and so should not be considered as limiting.

Referring back to equations (3) and (4), the stack difference may introduce three additional terms in each of equations (3) and (4). The first term, $\Delta I_N$, indicates an actual change to the intensity of the respective signal. The second term, $\Delta C_N$, indicates an actual change to the contrast of the respective signal. The third term, $\Delta \beta$, indicates an actual change to the phase of the respective signal. The three terms are dependent on the wavelength and/or the polarization of the measurement radiation beams 1210 and 1215. So, in the presence of a stack difference, the −1$^{st}$ diffraction order signal diffracted by the first periodic structure 1201, $I_{-1}^{+d}$, and the +1$^{st}$ diffraction order signal diffracted by the first periodic structure 1201, $I'_{+1}^{+d}$, may be collectively expressed by:

$$I_{\pm 1}^{+d} = (1+\Delta I_N)^* \{1 + C^*(1+\Delta C_N)^* \cos[(\beta + \Delta \beta) \pm 100_{+}]\}. \quad (5)$$

As mentioned above, an example for stack difference or target design is a difference in pitch, i.e., pitch difference between the first periodic structure 1201 relative to the second periodic structure 1206. According to equations (1) through (5), swing curves of stack sensitivity is a function of target design. Appropriate adjustments could be made for different target design parameters, such as pitch, CD, side wall angles, target profiles etc., and multiple design parameters may be adjusted concurrently.

Figure 15:
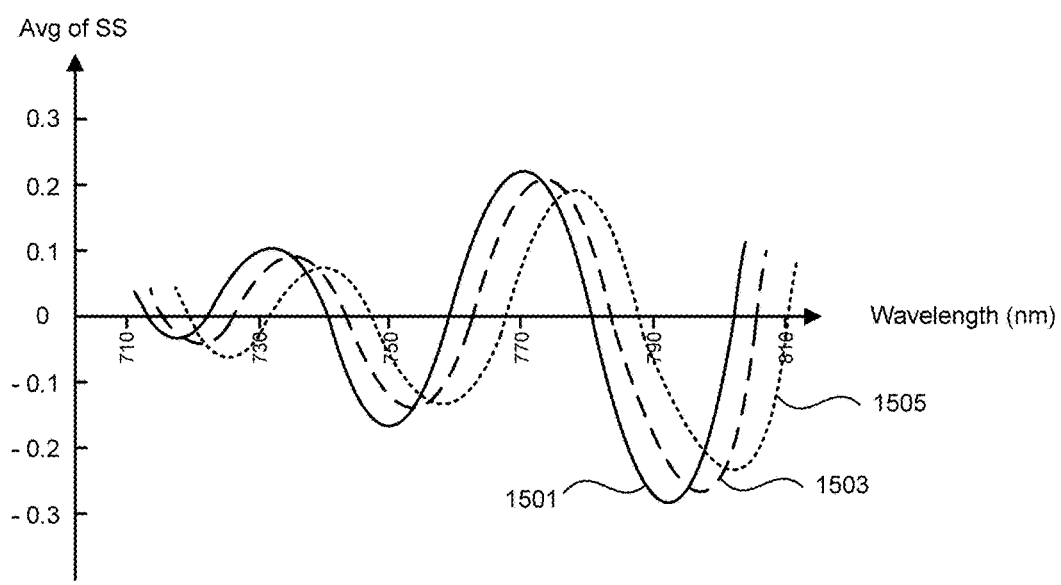
FIG. 15 illustrates an example graph of stack sensitivity as a function of incident radiation wavelength for different metrology target designs, according to an embodiment.

FIG. 15 shows various swing curves with respect to modified target pitches, while other target design parameters are kept constant in this example solely for the sake of simplicity, according to an embodiment. Using targets similar to those described in FIGS. 4, 13, and 14, a cluster of targets have been fabricated with target pitches varying over a range of 600 nm and 740 nm. Curves 1501, 1503, and 1505 are chosen to be shown here among a plurality of plots, with each curve plotted for stack sensitivity with respect to incident radiation wavelength for target pitches of 600 nm, 620 nm, and 640 nm, respectively. It should be noted that these pitches, wavelengths and resulting swing curves are selected only as examples and should not be considered as limiting. As target pitch varies, amplitude of the swing curves changes and the peaks (maximum stack sensitivity) also shifts horizontally along the x axis (incident radiation wavelength). As a result, for a specific incident radiation wavelength, there could be a desired target design that has a maximum stack sensitivity. Alternatively, a desired incident radiation wavelength can be determined for each target design at which stack sensitivity reaches maximum. Similarly, for a specific incident radiation polarization, there could be a desired target design that has a maximum stack sensitivity. Alternatively, a desired incident radiation polarization can be determined for each target design at which stack sensitivity reaches maximum.

The metrology target described above is also designed for one or more particular layers associated with a particular process stack (i.e., the process stack being the processes and material used to construct a particular device or part thereof for the layer, e.g., the one or material layers involved (e.g., the thickness and/or material type thereof), the lithographic exposure process, the resist development process, the bake process, the etch process, etc.) with the flexibility that the metrology target will provide measurement robustness for nominal changes in the process stack. That is, the metrology target is designed using knowledge of the process layers (e.g., their material, thickness, etc.), process variations, or the processing steps applied to the layers, etc. to arrive at a metrology target that will give optimal measurement results for the lithographic process parameter being measured.

As mentioned above, a metrology target measurement is most robust and reliable when the absolute value of stack sensitivity or K value is at maximum for a specific incident radiation wavelength, polarization, or process stack.

Figure 16:
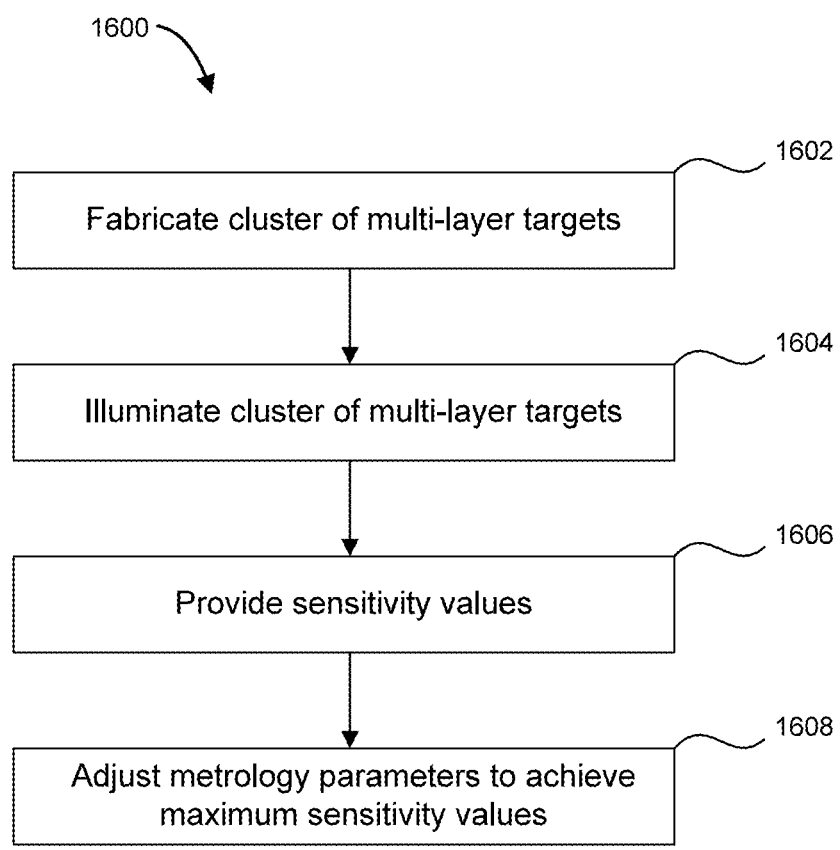
FIG. 16 is a flowchart of steps of a method for improving robustness and measurability of metrology target stacks, according to an embodiment.

FIG. 16 is a flow diagram of an illustrative method 1600 of improving robustness and measurability of metrology target stacks, in accordance with an embodiment of this present disclosure. Other method steps may be performed between the various steps of method 1600, and are omitted merely for clarity. Not all steps of method 1600 described below may be required, and in certain circumstances the steps may not be performed in the order shown.

Method 1600 begins with step 1602 where a number of N multi-layer targets are fabricated on the wafer for use in any appropriate lithography/metrology equipment. Examples of target design and construction are described above with reference to FIG. 3 or 7A-7B. The number of multi-layer targets N is not limited to four as shown in FIG. 3 and may be selected based on measurement needs. The multi-layer targets may be clustered at one location on the wafer, or may be placed at different locations to investigate target properties across a larger area on the wafer. The multi-layer targets' design may vary between each target by modifying one or more geometrical or fabrication parameters, including, but not limited to, pitch, CD, sub-segmentation, sidewall angle, duty cycle of the line and spaces, height, width, material, etc.

Method 1600 continues with step 1604, where the multi-layer targets are illuminated with an incident illumination radiation. The incident illumination radiation may comprise a variation of wavelengths, polarizations, or beam profiles etc. The illumination profile may be determined based on the metrology target design. Overlay measurements for each of the metrology targets are extracted from a difference in the light intensity for the first positive and negative first diffracted order reflected from the metrology targets.

Method 1600 continues with step 1606, at which at least a number of N stack sensitivity values $K_i$, where $i \in [1, N]$, from the cluster of multi-layer targets are determined based on the overlay measurements. The determination of stack sensitivity values $K_i$ may be performed by a computer processor using a computer-implemented method. As described above, stack sensitivity or K value may vary across the wafer due to process perturbations, and may be different between each of the multi-layer targets. Therefore each multi-layer target $T_i$ has a K value of $K_i$, where $i \in [1, N]$.

Method 1600 continues with step 1608, where the metrology parameters of the multi-layer target are selected or adjusted to achieve a large K value. The determination of the metrology parameters may be performed by a computer processor using a computer-implemented method. The metrology parameters may include and are not limited to geometrical or fabrication parameters, for example, pitch, CD, sub-segmentation, sidewall angle, duty cycle of the line and spaces, height, width, refraction index, etc. A simulation package may be used to select or adjust the metrology parameters of the multi-layer target design such that a maximum K value is achieved to provide the most robust and reliable measurement. An example for the simulation package may include an overarching methodology that is referred to as "Design for Control", abbreviated as D4C. Further details of D4C can be found in United State Patent Publication U.S. 20160140267, which is hereby incorporated by reference in its entirety.

Based on the determination process described above with reference to method 1600, processing parameters of the metrology system may also be calibrated to achieve the most robust and reliable measurement. For example, processing parameters such as a wavelength of radiation used in the metrology system for the target, polarization of radiation used in the metrology system, numerical aperture of the metrology system, may be adjusted.

Figure 17A:
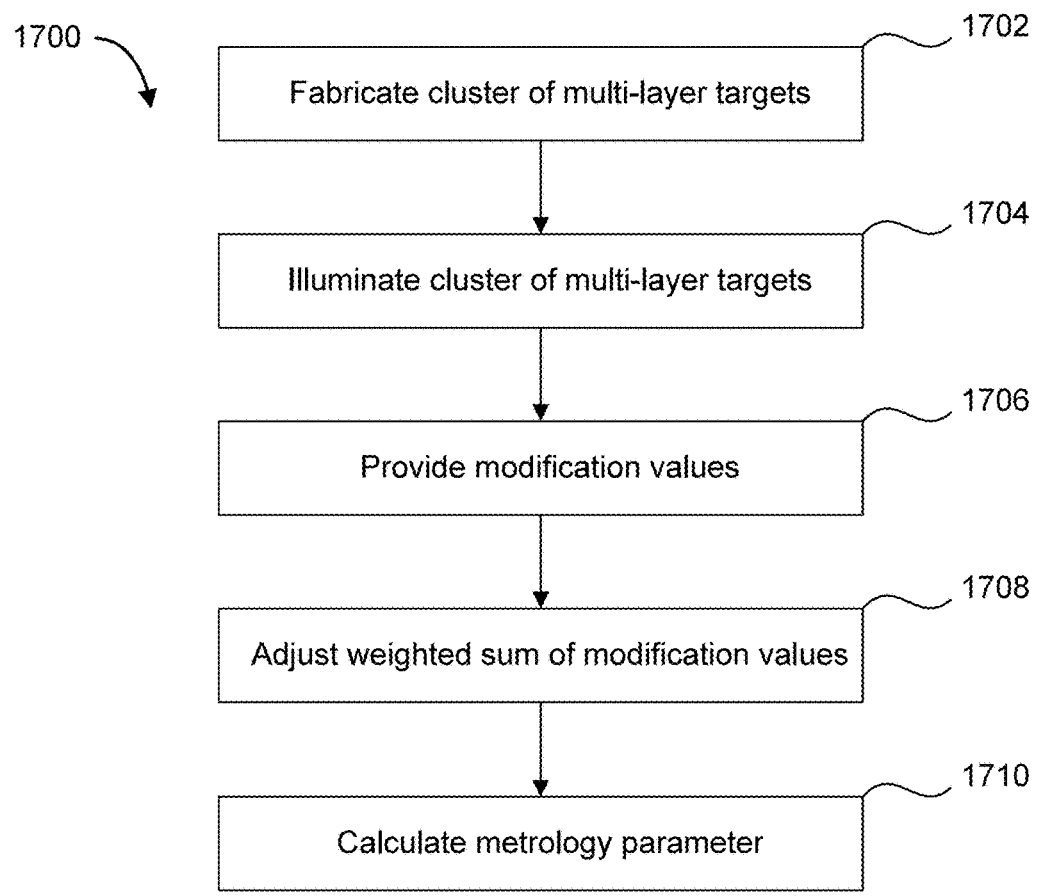
FIG. 17A is a flowchart of steps of a method for improving robustness and measurability of metrology target stacks, according to another embodiment.

FIG. 17A is a flow diagram of an illustrative method 1700 of improving robustness and measurability of metrology target stacks, in accordance with another embodiment of the present disclosure. Other method steps may be performed between the various steps of method 1700, and are omitted merely for clarity. Not all steps of method 1700 described below may be required, and in some circumstances the steps can be performed in a different order.

Figure 17B:
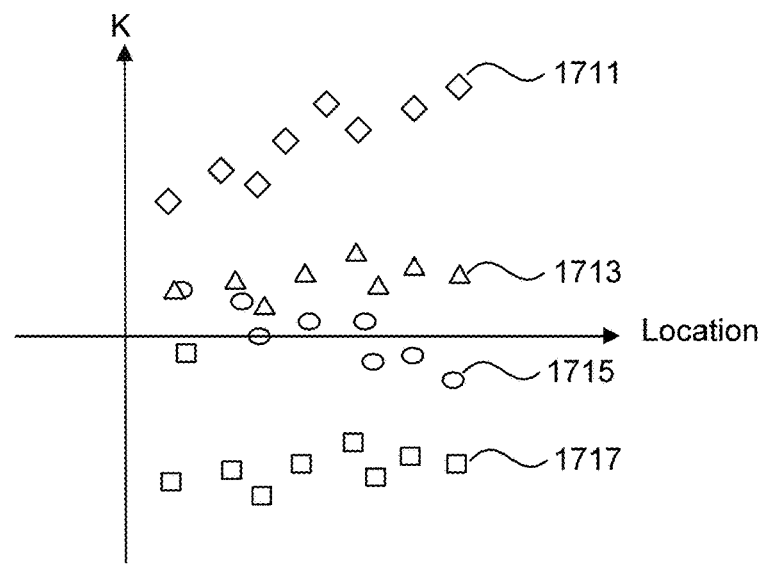
FIG. 17B is an example graph of K value as a function of metrology target locations for different metrology target designs, according to an embodiment.

FIG. 17B is an exemplary graph of K value as a function of metrology target locations for different metrology target designs, according to an embodiment.

Method 1700 begins with step 1702 where a number of N multi-layer targets are fabricated on the wafer by any appropriate lithography/metrology equipment. Similar to the metrology target design described in step 1602 above, the metrology parameters of the multi-layer targets may include, and are not limited to, geometrical or fabrication parameters, for example, pitch, CD, sub-segmentation, sidewall angle, duty cycle of the line and spaces, height, width, refraction index, etc. Clusters of multi-layer targets may be formed on different areas across the wafer, while each area may comprise multiple targets with different designs. Therefore it is possible to simultaneously have similarly designed targets placed across the wafer surface while also have targets with different designs placed in close proximity at a specific region on the wafer.

Method 1700 continues with step 1704, where the multi-layer targets are illuminated with an incident illumination radiation. The incident illumination radiation may comprise a variation of wavelengths, polarizations, or beam profiles etc., and the illumination profile may be determined based on the metrology target design. Overlay measurements for each of the metrology targets are extracted from a difference in the light intensity for the first positive and negative first diffracted order reflected from the metrology targets.

Method 1700 continues with step 1706, at which at least a number of N stack sensitivity values $K_i$, where $i \in [1, N]$, from the cluster of multi-layer targets are determined based on the overlay measurements. The determination of stack sensitivity values $K_i$ may be performed by a computer processor using a computer-implemented method. As described above, stack sensitivity or K value may vary across the wafer due to process perturbations, and may be different between each of the multi-layer targets. Therefore each multi-layer target $T_i$ has a K value of $K_i$ and assigned a multiplication factor $\alpha_i$, where $i \in [1, N]$. It should be noted that sensitivity values are hereby presented as exemplary modification (or optimization) parameters, and any appropriate modification parameter with any reference value may be used, for example but not limited to, target coefficient or overlay error. Multiplication factor $\alpha_i$ is a coefficient that can be modified based on processing condition, and can be the result of any correlation analysis, such as Principal Component Analysis (PCA). Different methods of correlation analysis may be used, and PCA analysis is referred to herein purely as one example. PCA is a mathematical procedure well-known in the art and need not be discussed in detail here.

Method 1700 continues with step 1708, where the weighted sum of $K_i$ is adjusted to reach a maximum value. The determination and optimization of stack sensitivity values $K_i$ may be performed by a computer processor using a computer-implemented method. In accordance with an embodiment of the present disclosure, the metrology target measurement is most robust and reliable when $\Sigma_{i=1}^{N} \alpha_i * K_i$ reaches maximum value, while $\Sigma_{i=1} \alpha_i = 1$ and $\alpha_i \in [-1, 1]$. For example, larger multiplication factors such as $\alpha_i = 1$ may be assigned to target measurements with higher sensitivity values such that they are given more weight in the calculated sum, while lower multiplication factors such as $\alpha_i = -1$ may be assigned to target measurements with lower sensitivity values such that they are given less weight in the calculated sum. Referring to FIG. 17B as an example, K values are measured for various target designs at various locations across the wafer. At a specific location, K values 1711, 1713, 1715, and 1717 are determined for metrology targets 1711', 1713', 1715', and 1717' (not shown), respectively. It is to be understood that the K values or metrology targets herein are for the purpose of description by example and not of limitation, and there may be a plurality of metrology targets with different designs formed on the wafer. A large multiplication factor $\alpha_i=1$ is assigned to K value 1711 since it has a high sensitivity value. Similarly, a low multiplication factor $\alpha_i=-1$ is assigned to K value 1717 since it has a low sensitivity value. The determination of multiplication factors may also depend on the correlation between the optimization factor and any target properties, such as location, stack indicators, pitch, CD, sub-segmentation, sidewall angle, duty cycle of the line and spaces, height, width, material, etc. As mentioned above, different methods of correlation analysis may be used.

Method 1700 continues with step 1710, where the metrology parameters of the multi-layer targets can be calculated. The final metrology parameter value for the cluster of N multi-layer targets is a linear combination of metrology parameter $P_i$ measured for each multi-layer target, as shown in the equation below:

$$P=\Sigma_{i=1}^{N}\alpha_i*P_i \quad (6)$$

where $i \in [1, N]$. Therefore the final metrology parameter P can be modified (or optimized) based on the linear combination of individual metrology parameter $P_i$ calculated from each multi-layer target and multiplication factor $\alpha_i$.

Based on the determination process described above with reference to method 1700, metrology target designs, such as gratings design, can be further modified to accommodate a variety of lithography processes and process perturbations, and achieve maximized robustness and measurability. For example, methods and systems for automatically generating robust metrology targets include D4C.

Based on the determination process described above with reference to method 1700, processing parameters of the lithography system may be calibrated to achieve the most robust and reliable measurement. For example, processing parameters such as a wavelength of radiation used in the metrology system for the target, polarization of radiation used in the metrology system, numerical aperture of the metrology system, may be adjusted based on the stack sensitivity measurement from the metrology targets.

Figure 18A:
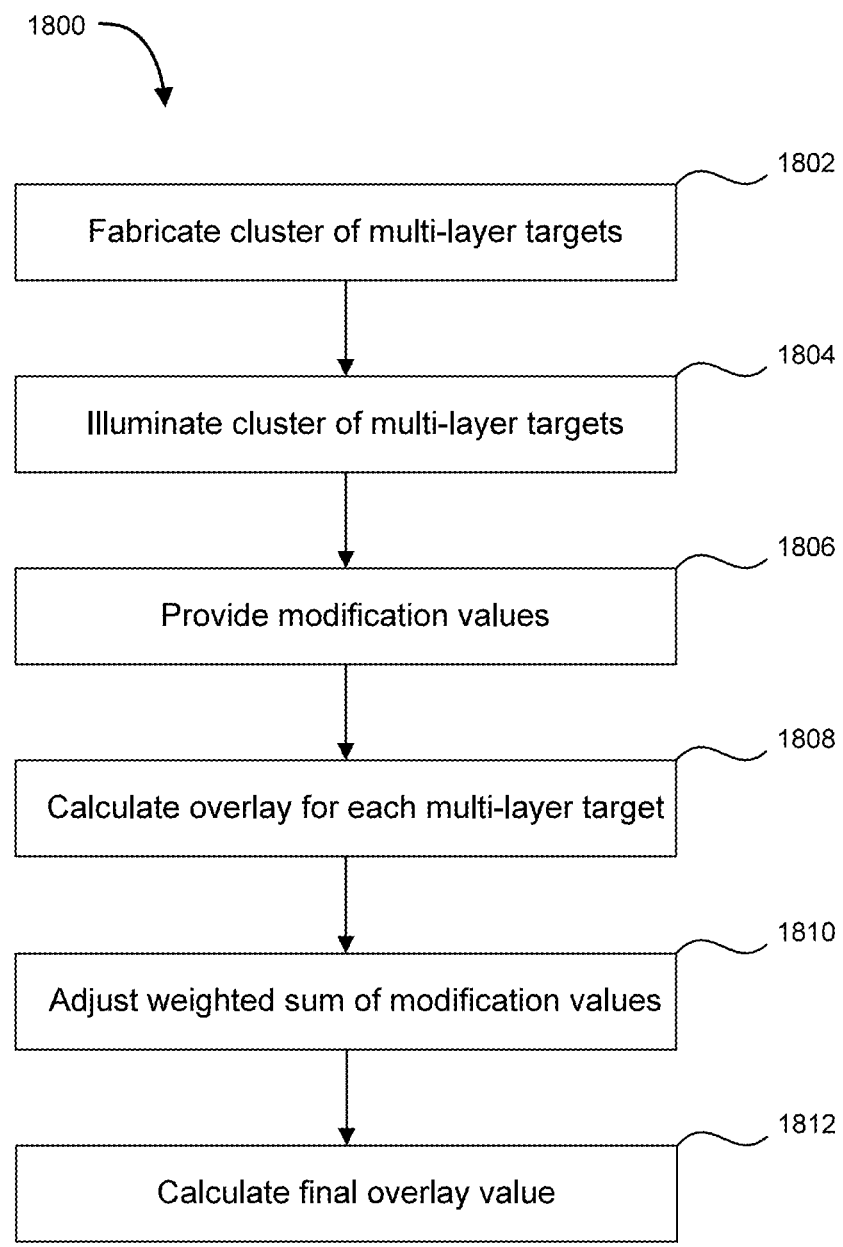
FIG. 18A is a flowchart of steps of a method for improving robustness and measurability of metrology target stacks, according to a further embodiment.

FIG. 18A is a flow diagram of an illustrative method 1800 of improving robustness and measurability of overlay in metrology target stacks, in accordance with a further embodiment of the present disclosure. Other method steps may be performed between the various steps of method 1800, and are omitted merely for clarity. Not all steps of method 1800 described below may be required, and in some circumstances the steps can be performed in a different order.

Figure 18B:
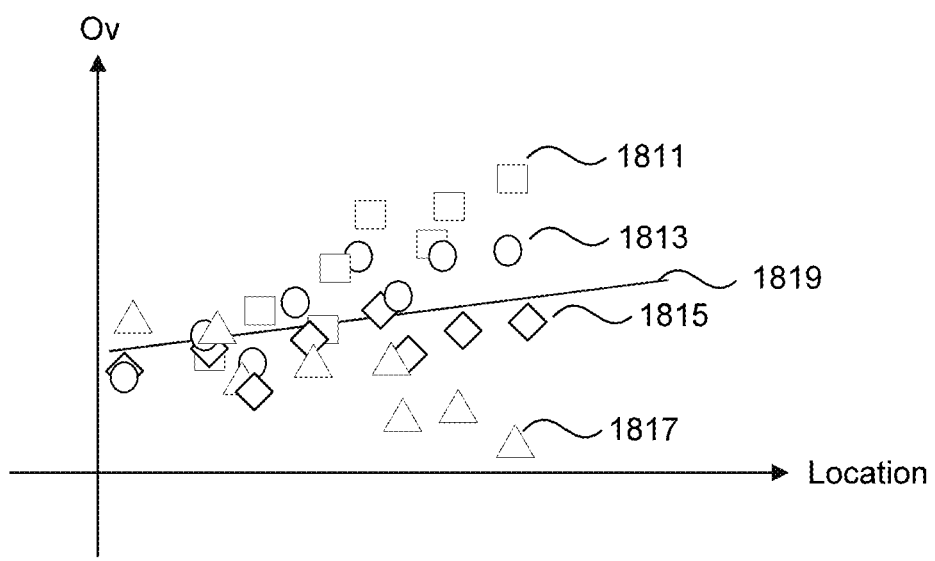
FIG. 18B is an example graph of overlay value as a function of metrology target locations for different metrology target designs, according to an embodiment.

FIG. 18B is an example graph of overlay value as a function of metrology target locations for different metrology target designs, according to an embodiment.

Method 1800 begins with step 1802 where a number of N multi-layer targets are fabricated on the wafer for use in an overlay measurement method by the inspection apparatus of FIG. 3, or by any appropriate lithography/metrology equipment. Similar to the metrology target design described in step 1602 above, the design may vary between each multi-layer target by modifying one or more geometrical or fabrication parameters, including, but not limited to, pitch, CD, sub-segmentation, sidewall angle, duty cycle of the line and spaces, height, width, refraction index, etc. As noted above, clusters of multi-layer targets may be formed on different areas across the wafer, while each area may comprise multiple targets with different designs.

Method 1800 continues with step 1804, where the multi-layer targets are illuminated with an incident illumination radiation. The incident illumination radiation may comprise a variation of wavelengths, polarizations, or beam profiles etc. The illumination profile may be determined based on the metrology target design. Overlay measurements for each of the metrology targets are extracted from a difference in the light intensities for the positive and negative first diffraction orders of scattered light from the metrology targets.

Method 1800 continues with step 1806, at which at least a number of N stack sensitivity values $K_i$, where $i \in [1, N]$, from the cluster of multi-layer targets are determined based on the overlay measurements. The determination of stack sensitivity values $K_i$ may be performed by a computer processor using a computer-implemented method. As described above, stack sensitivity or K value may vary across the wafer due to process perturbations, and may be different between each of the multi-layer targets. Therefore each multi-layer target $T_i$ has a K value of $K_i$. As noted above, stack sensitivity values are hereby presented as exemplary modification values, and any appropriate modification values with any reference value may be used.

Method 1800 continues with step 1808, where the overlay value $OV_i$ for each multi-layer target $T_i$ is calculated by using equation (2) from above and $$K_i = \frac{A_{+d} + A_{-d}}{2d}.$$

Each sensitivity value $K_i$ is assigned a multiplication factor $\alpha_i^{OV}$, where $i \in [1, N]$. Multiplication factor $\alpha_i^{OV}$ is a coefficient that can be modified based on processing condition and external reference overlay value, and can also be the result of any correlation analysis, such as Principal Component Analysis (PCA). As mentioned above, different methods of correlation analysis may be used, and PCA analysis is referred to herein merely as one example.

Method 1800 continues with step 1810, where the weighted sum of stack sensitivity values is adjusted. The determination and optimization of the stack sensitivity values may be performed by a computer processor using a computer-implemented method. In accordance with an embodiment of the present disclosure, the metrology target measurement is most robust and reliable when $\Sigma_{i=1}^{N}\alpha_i^{OV}*K_i$ reaches maximum value.

Multiplication factors $\alpha_i^{OV}$ can be further adjusted based on external reference overlay values to provide a more accurate measurement of the final overlay value. An exemplary method of optimizing (or modifying) final overlay value OV using an external reference overlay value is hereby described with reference to FIG. 18B. It is to be understood that the overlay values or metrology targets herein are for the purpose of description by example and not of limitation, and there may be a plurality of metrology targets with different designs formed on the wafer. Overlay values are measured for various target designs at various locations across the wafer. At a specific location, overlay values 1811, 1813, 1815, and 1817 are determined for targets 1811', 1813', 1815', and 1817' (not shown), respectively. For example, if the overlay values of a number of multi-layer targets $T_i$ are systematically off from an external reference overlay value 1819, each individual multiplication factor $\alpha_i^{OV}$ can also be adjusted based on the difference between the corresponding overlay value and the external reference overlay value. As a result, multi-layer targets that have overlay values closer to the external reference overlay value 1819 may have a relatively higher multiplication factor $\alpha_i^{OV}$ such that they are given more weight in the calculated sum, while multi-layer targets that have overlay values deviate away from the external reference overlay value may have a relatively lower multiplication factor $\alpha_i^{OV}$, such that they are given less weight in the calculated sum. For example, a low multiplication factor $\alpha_i^{OV}=0.6$ will be assigned to overlay value 1811 since it has a relatively large difference between external reference sensitivity value 1819. Similarly, a high multiplication factor $\alpha_i^{OV}=1.2$ will be assigned to overlay value 1815 since it has a relatively small difference between external reference sensitivity value 1819. Therefore the final overlay value OV can be further optimized (or modified) based on the linear combination of individual overlay value calculations from each multi-layer targets, providing a more robust measuring process than using a single target.

Method 1800 continues with step 1812, where the final overlay value OV for the cluster of N multi-layer targets is calculated through a linear combination of each overlay value $OV_i$ via the equation below:

$$OV = \sum_{i=1}^{N} \alpha_i^{OV} * OV_i \qquad (6)$$

where $i \in [1, N]$. Therefore the final overlay value OV can be optimized (or modified) based on the linear combination of individual overlay value calculations from each multi-layer targets.

Similarly, final overlay value OV can also be optimized (or modified) based on multiplication factor $\alpha_i$ and an external reference overlay value obtained from an external source, such as CD-SEM measurement or Holistic Metrology Qualification (HMQ) estimate. Further details of HMQ can be found in PCT Application WO 2015/018625 A1, which is hereby incorporated by reference herein in its entirety.

Based on the determination process of final overlay value OV described above, appropriate metrology target designs can be selected or further modified to accommodate a variety of lithography processes and process perturbations, and achieve maximized robustness and measurability. For example, methods and systems for automatically generating robust metrology targets include D4C.

Based on the determination process described above with reference to method 1800, processing parameters of the lithography system may be calibrated to achieve the most robust and reliable measurement. For example, processing parameters such as a wavelength of radiation used in the metrology system for the target, polarization of radiation used in the metrology system, numerical aperture of the metrology system, may be adjusted.

Figure 19:
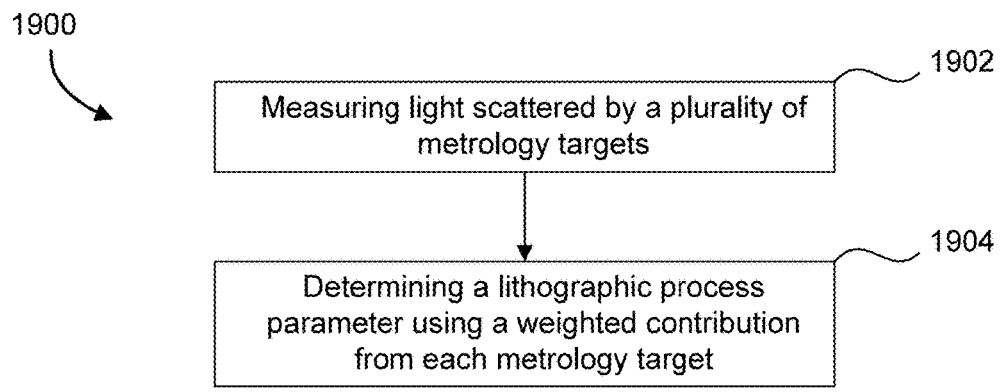
FIG. 19 is a flowchart of steps of a method for measuring a lithography process parameter using metrology targets, according to an embodiment.

FIG. 19 is a flow diagram of an illustrative method 1900 of measuring a lithography process parameter using metrology targets, in accordance with an embodiment of this present disclosure. Other method steps may be performed between the various steps of method 1900, and are omitted merely for clarity. Not all steps of method 1900 described below may be required, and in certain circumstances the steps may not be performed in the order shown.

Method 1900 begins with step 1902, where light scattered by a plurality of metrology targets is measured. The plurality of metrology target may be illuminated with an incident radiation, the incident radiation having an illumination profile such as wavelength or polarization. The measurement of scattered light is performed in optical instruments such as scatterometers or other metrology tools. The plurality of metrology targets are designed using metrology parameters and produced by a manufacturing process. Examples of metrology parameters are, but not limited to, the pitch of the gratings used to form the metrology target, CD, angle of the lines forming the gratings, duty cycle of lines and spaces forming the grating. An example of the manufacturing process is, but not limited to, a lithographic manufacturing process using a lithographic projection apparatus. a pattern (e.g. in a mask) is imaged onto a substrate that is at least partially covered by a layer of radiation-sensitive material (resist). Prior to this imaging step, the substrate may undergo various procedures, such as priming, resist coating and a soft bake. After exposure, the substrate may be subjected to other procedures, such as a post-exposure bake (PEB), development, a hard bake and measurement/inspection of the imaged features. This array of procedures is used as a basis to pattern an individual layer of a device, e.g. a metrology target or an IC. Such a patterned layer may then undergo various processes such as etching, ion-implantation (doping), metallization, oxidation, chemo-mechanical polishing, etc., all intended to finish off an individual layer.

Method 1900 continues with step 1904, where a lithographic process parameter for the plurality of metrology targets is determined using a weighted contribution from each metrology target.

The weighted contribution from each metrology target may be determined using a method similar to method 1700, where modification values are determined for each metrology target based on their respective scattered light measurements, and a multiplication value is determined for each modification value. The multiplication factors are determined by calculating and maximizing a sum of the multiplication factors multiplied by their corresponding modification values. For example, larger multiplication factors may be assigned to target measurements with higher modification values such that they are given more weight in the calculated sum, while lower multiplication factors may be assigned to target measurements with lower modification values such that they are given less weight in the calculated sum. An individual lithographic process parameter for each metrology target is also determined, and these individual lithographic process parameters are used to determine the lithographic process parameter for the plurality of metrology targets by calculating a sum of the determined multiplication factors multiplied by their corresponding individual lithographic process parameters.

Alternatively, the weighted contribution from each metrology target may be determined using a method similar to method 1800, where multiplication values are further determined using a reference lithographic process parameter. First, modification values are determined for each metrology target of the plurality of metrology targets based on their scattered light measurements, and a multiplication value is determined for each modification value by maximizing a sum of the multiplication factors multiplied by their corresponding modification values. Then the multiplication factors are further adjusted by determining an individual lithographic process parameter for each metrology target, and adjusting the multiplication factors based on differences between the reference lithographic process parameter and their corresponding individual lithographic process parameters. The lithographic process parameter is then determined by determining a sum of the multiplication factors multiplied by their corresponding individual lithographic process parameters.

Figure 20:
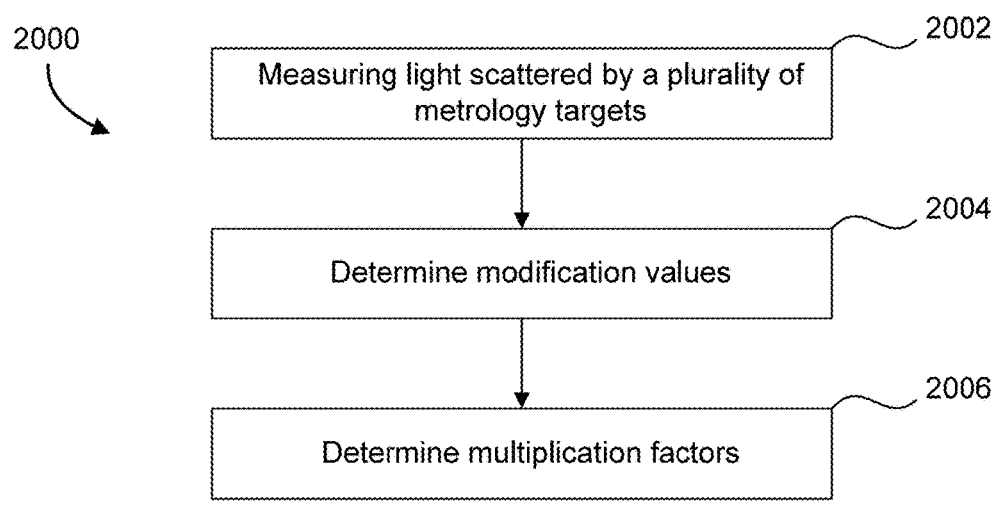
FIG. 20 is a flowchart of steps of a method for metrology system calibration using metrology targets, according to an embodiment.

FIG. 20 is a flow diagram of an illustrative method 2000 for metrology system calibration using metrology targets, in accordance with an embodiment of this present disclosure. Other method steps may be performed between the various steps of method 2000, and are omitted merely for clarity. Not all steps of method 2000 described below may be required, and in certain circumstances the steps may not be performed in the order shown.

Method 2000 begins with step 2002, where light scattered by a plurality of metrology targets is measured. Similar to method 1900, the plurality of metrology target may be illuminated with an incident radiation having an illumination profile such as wavelength or polarization. The measurement of scattered light is performed in optical instruments such as scatterometers or other metrology tools. The plurality of metrology targets are designed using metrology parameters and produced by a manufacturing process.

Method 2000 continues with step 2004, where a modification value is determined for each metrology target using their scattered light measurements. Therefore each multi-layer target has a determined modification value and a multiplication factor. Examples of modification values include, but not limited to, stack sensitivity, target coefficient, or overlay error.

Method 2000 continues with step 2006, where multiplication factors are determined by calculating and maximizing a sum of the multiplication factors multiplied by their corresponding modification values. Similar to method 1700, the multiplication factors are determined by calculating and maximizing a sum of the multiplication factors multiplied by their corresponding modification values. For example, larger multiplication factors may be assigned to target measurements with higher modification values such that they are given more weight in the calculated sum, while lower multiplication factors may be assigned to target measurements with lower modification values such that they are given less weight in the calculated sum. Measurement processes can be calibrated by using the determined multiplication factors and their corresponding metrology targets.

Using the metrology targets that provide higher modification values, processing parameters of the metrology system may also be calibrated to achieve the most robust and reliable measurement. For example, processing parameters under which metrology targets with high modification values are designed to provide the most robust measurement can be selected for subsequent measurements. Processing parameters include, but not limited to, wavelengths or polarizations of incident radiation used in the metrology system for metrology target measurement, process stack configuration, or numerical aperture of the metrology system.

Figure 21:
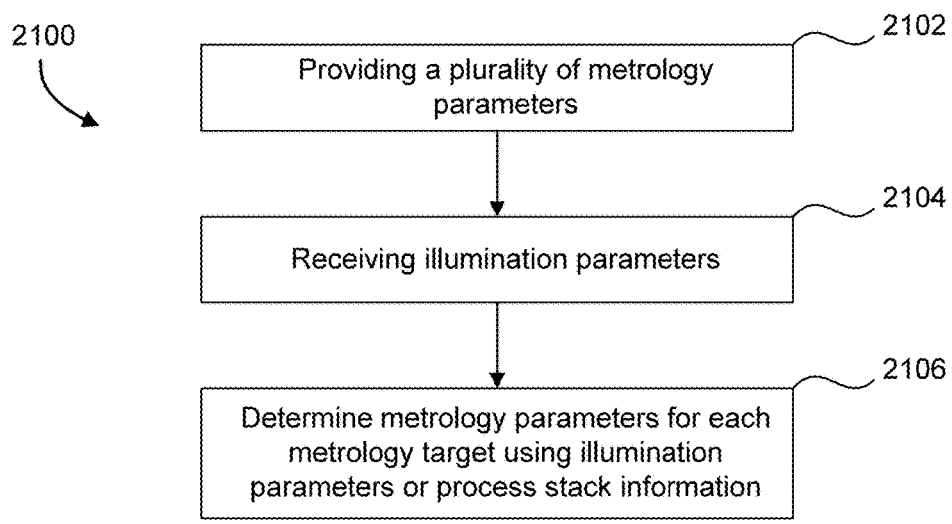
FIG. 21 is a flowchart of steps of a method for designing metrology targets, according to an embodiment.

FIG. 21 is a flow diagram of an illustrative method 2100 for metrology target design, in accordance with an embodiment of this present disclosure. Other method steps may be performed between the various steps of method 2100, and are omitted merely for clarity. Not all steps of method 2100 described below may be required, and in certain circumstances the steps may not be performed in the order shown.

Method 2100 begins with step 2102, where a plurality of metrology parameters is provided to a computer apparatus for generating a plurality of metrology targets designs corresponding to a plurality of metrology targets. Similar to the metrology targets described in method 1700, metrology parameters are geometrical or fabrication parameters for the metrology targets, and examples are, but not limited to, pitch, CD, sub-segmentation, sidewall angle, duty cycle of the line and spaces, height, width, refraction index, etc. Each metrology target is designed to be respectively disposed at a different location on a substrate. As described above with reference to FIG. 5, there is a plurality of composite targets placed at different locations on substrate W such that measurements and information about desired areas on substrate W can be obtained. Therefore, clusters of multi-layer targets may be formed on different areas across the wafer, while each area may comprise multiple sub-targets with different designs. It is possible to simultaneously have similarly designed targets placed across the wafer surface while also have targets with different designs placed in close proximity at a specific region on the wafer.

Method 2100 continues with step 2104, where illumination parameters for the incident radiation used to measure the plurality of metrology targets are received in the computer apparatus. The illumination parameters may comprise a variation of wavelengths, polarizations, or beam profiles etc.

Method 2100 continues with step 2106, where the computer apparatus determines the metrology parameters for each metrology target using the illumination parameters or process stack information of the substrate. The metrology parameters are determined such that a selection of different metrology targets will provide different measurement results under incident radiations or process stack configurations. As described above with reference to FIG. 15, there could be a desired target design that provides a maximum stack sensitivity for a specific illumination parameter or process stack. For example, a target design may be determined such that stack sensitivity reaches maximum for a measurement using a desired incident radiation wavelength or polarization. Similarly, a target design may be determined such that stack sensitivity reaches maximum for a desired incident process stack.

Figure 22:
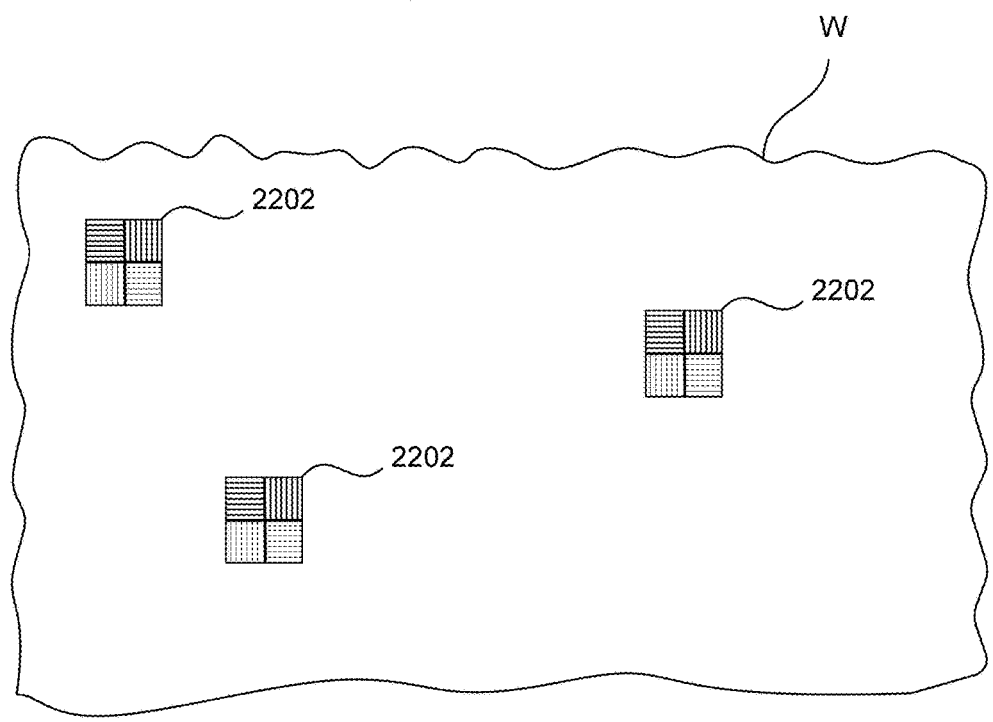
FIG. 22 is a schematic illustration of a form of multi-grating metrology targets, according to an embodiment.

FIG. 22 schematically depicts a form of multi-grating metrology targets disposed on a substrate by a manufacturing process, in accordance with an embodiment of this present disclosure. Similar to the composite targets described with reference to FIG. 5, multi-grating metrology target 2202 comprises at least two sub-targets positioned closely together so that they will all be within a measurement spot formed by the illumination beam of the metrology apparatus. The two sub-targets have different geometrical or fabrication parameters, for example, pitch, CD, sub-segmentation, sidewall angle, duty cycle of the line and spaces, height, width, refraction index, etc. This can be achieved by adjusting metrology parameters used to design the metrology targets. Designs of the sub-targets are determined such that stack sensitivity of a sub-target reaches maximum for a desired incident radiation wavelength or polarization. Similarly, a sub-target design may be determined such that stack sensitivity reaches maximum for a desired incident process stack. Therefore the metrology targets provide different measurement sensitivity under various incident radiations or process stack configurations.

A plurality of multi-grating metrology target 2202 are placed at different locations on substrate W. Location choices are determined based on measurement needs, such as but not limited to, whether measurement information is needed for that location of substrate W or to eliminate process variation effects on metrology measurements, such as stack depth variation effects. Therefore it is possible to simultaneously have similarly designed metrology targets each with a plurality of sub-targets placed across the wafer surface, while also have targets with different designs placed in close proximity at a specific region on the wafer.

While the target structures described herein are metrology targets specifically designed and formed for the purposes of measurement, in other embodiments, properties may be measured on targets which are functional parts of devices formed on the substrate. Many devices have regular, grating-like structures. The terms 'target', 'target grating' and 'target structure' as used herein do not require that the structure has been provided specifically for the measurement being performed.

While overlay targets in the form of gratings have been described, in an embodiment, other target types may be used such as box-in-box image based overlay targets.

While metrology targets to determine overlay have been primarily described, the metrology targets may be used to determine, in the alternative or additionally, one of more other characteristics, such as focus, dose, etc.

The metrology targets according to an embodiment may be defined using a data structure such as a pixel-based data structure or a polygon-based data structure. The polygon-based data structure may, for example, be described using GDSII data formats, which are rather common in the chip manufacturing industry. Still, any suitable data structure or data format may be used without departing from the scope of the embodiments. The metrology targets may be stored in a database from which a user may select the required metrology target for use in a particular semiconductor processing step. Such a database may comprise a single metrology target or a plurality of metrology targets selected or identified according to the embodiment. The database may also comprise a plurality of metrology targets in which the database comprises additional information for each of the plurality of metrology targets. This additional information may comprise, for example, information related to a suitability and/or a quality of the metrology target for a specific lithographic process step and may even include suitability and/or quality of a single metrology target to different lithographic process steps. The suitability and/or quality of the metrology target may be expressed in a suitability value and/or a quality value, respectively, or any other value which may be used during a selection process of selecting one metrology target from the database which is to be used for the specific lithographic process step.

In an embodiment, the computer readable medium may comprise instructions for activating at least some of the method steps using a connection to the computer readable medium from a remote computer or from a remote system. Such connection may, for example, be generated over a secure network or via a (secure) connection over the world-wide-web (internet). In this embodiment, users may, for example, log in from a remote location to use the computer readable medium for determining a suitability and/or a quality of the metrology target design. The proposed metrology target design may be provided by the remote computer (or by an operator using the remote computer to provide the metrology target design to the system for determining the suitability of the metrology target design). So the proposed metrology target design which is to be simulated using models may be owned by a different entity or company compared to the models used during the simulation process. Subsequently, the resulting determined suitability to evaluate the metrology target quality may be provided back to the remote computer, for example, without leaving any residual details to excess the proposed metrology target design or the simulation parameters used. In such an embodiment, a customer may acquire the option to run an assessment of individually proposed metrology target designs without owning the software or having a copy of the software at its remote location. Such option may be obtained by, for example, a user agreement. A benefit of such user agreement may be that the models used in the simulations may always be the most recent and/or the most detailed models available without the need to locally update any software. Furthermore, by separating the model simulation and the proposed metrology target proposal, the details of the designed markers or the different layers used for the processing need not to be shared by the two companies.

In association with the physical grating structures of the targets as realized on substrates and patterning devices, an embodiment may include a computer program containing one or more sequences of machine-readable instructions describing a method of designing a target, producing a target on a substrate, measuring a target on a substrate and/or analyzing measurements to obtain information about a lithographic process. This computer program may be executed for example within unit PU in the apparatus of FIGS. 3 and 4 and/or the control unit LACU of FIG. 2. There may also be provided a data storage medium (e.g., semiconductor memory, magnetic or optical disk) having such a computer program stored therein. Where an existing apparatus, for example of the type shown in FIGS. 1-4, is already in production and/or in use, an embodiment can be implemented by the provision of updated computer program products for causing a processor of the apparatus to perform a method as described herein.

An embodiment of the invention may take the form of a computer program containing one or more sequences of machine-readable instructions describing a method as disclosed herein, or a data storage medium (e.g. semiconductor memory, magnetic or optical disk) having such a computer program stored therein. Further, the machine readable instruction may be embodied in two or more computer programs. The two or more computer programs may be stored on one or more different memories and/or data storage media.

Any controllers described herein may each or in combination be operable when the one or more computer programs are read by one or more computer processors located within at least one component of the lithographic apparatus. The controllers may each or in combination have any suitable configuration for receiving, processing, and sending signals. One or more processors are configured to communicate with the at least one of the controllers. For example, each controller may include one or more processors for executing the computer programs that include machine-readable instructions for the methods described above. The controllers may include data storage medium for storing such computer programs, and/or hardware to receive such medium. So the controller(s) may operate according the machine readable instructions of one or more computer programs.

The disclosure may further be described using the following clauses:

I. A method of metrology target design, the method comprising:
  receiving an illumination parameter for measuring a metrology target and
  selecting and/or adjusting a metrology parameter associated with the metrology target design for enhancing an accuracy and/or a robustness of the measurement of the metrology target design using the illumination parameter.

II. A method to determine a parameter of a lithographic process comprising:
  receiving the light scattered from a region comprising at least two metrology targets optimized to provide a robust and optimal metrology measurement and determining the parameter of the lithographic process from a weighted contribution of each individual metrology targets.

Further embodiments according to the present invention are further described in below numbered clauses:

1. A method comprising:
measuring light scattered by a plurality of metrology targets, the plurality of metrology targets having been designed using metrology parameters and produced by a manufacturing process; and
determining a lithographic process parameter for the plurality of metrology targets using a weighted contribution from each metrology target.

2. The method of clause 1, wherein the weighted contribution is calculated by determining a modification value and a multiplication factor for each metrology target.

3. The method of clause 2, wherein determining the multiplication factors further comprises determining a sum of the multiplication factors multiplied by their corresponding modification values.

4. The method of clause 3, wherein determining the lithographic process parameter comprises adjusting the multiplication factors such that the sum is maximized.

5. The method of clause 4, wherein determining the lithographic process parameter further comprises determining an individual lithographic process parameters for each metrology target, and determining a sum of the multiplication factors multiplied by their corresponding individual lithographic process parameters.

6. The method of clause 1, wherein the modification values are target coefficients or overlay errors of the plurality of metrology targets.

7. The method of clause 1, wherein the modification values are stack sensitivity values of the plurality of metrology targets.

8. The method of clause 1, wherein the lithographic process parameters are overlay values.

9. The method of clause 1, wherein the metrology parameters comprise material choice, critical dimension, sub-segmentation, or sidewall angle.

10. The method of clause 1, wherein the plurality of metrology targets comprise multi-layer periodic structures.

11. The method of clause 10, wherein the metrology parameters of the multi-layer periodic structures comprise pitch, duty cycle of lines and spaces, height, or width.

12. The method of clause 1, wherein the plurality of metrology targets are designed for different wavelengths or polarizations of an incident radiation or process stacks.

13. The method of clause 1, wherein determining the lithographic process parameter further comprises using a reference lithographic process parameter.

14. The method of clause 13, wherein the weighted contribution is calculated by determining a modification value and a multiplication factor for each metrology target.

15. The method of clause 14, wherein the multiplication factors are determined using a sum of the multiplication factors multiplied by their corresponding modification values.

16. The method of clause 15, wherein the multiplication factors are further determined by determining an individual lithographic process parameter for each metrology target, and adjusting the multiplication factors based on differences between the reference lithographic process parameter and their corresponding individual lithographic process parameters.

17. The method of clause 16, wherein determining the lithographic process parameter further comprises determining a sum of the multiplication factors multiplied by their corresponding individual lithographic process parameters.

18. A method comprising:
measuring light scattered by a plurality of metrology targets, the plurality of metrology targets having been designed using metrology parameters and produced by a manufacturing process;
determining a modification value for each metrology target; and
determining a multiplication factor for each metrology target based on its corresponding modification value.

19. The method of clause 18, wherein determining the multiplication factors comprises determining a sum of the multiplication factors multiplied by their corresponding modification values.

20. The method of clause 19, wherein determining the multiplication factors further comprises adjusting the multiplication factors such that the sum is maximized.

21. The method of clause 18, wherein the modification values are target coefficients or overlay errors of the plurality of metrology targets.

22. The method of clause 18, wherein the modification values are stack sensitivity values of the plurality of metrology targets.

23. The method of clause 18, wherein the lithographic process parameters are overlay values.

24. The method of clause 18, wherein the metrology parameters comprise material choice, critical dimension, sub-segmentation, or sidewall angle.

25. The method of clause 18, wherein the plurality of metrology targets comprise multi-layer periodic structures.

26. The method of clause 25, wherein the metrology parameters of the multi-layer periodic structures comprise pitch, duty cycle of lines and spaces, height, or width.

27. The method of clause 18, wherein the plurality of metrology targets are designed for different wavelengths or polarizations of an incident radiation or process stacks.

28. A method of metrology target design, the method comprising:
providing a plurality of metrology parameters for generating a plurality of metrology targets designs corresponding to a plurality of metrology targets, wherein each metrology target is designed to be respectively disposed at a different location on a substrate;
receiving illumination parameters for measuring the plurality of metrology targets; and
determining, by a computer apparatus, the plurality of metrology parameters for each metrology target using the illumination parameters or process stack information of the substrate.

29. The method of clause 28, wherein the illumination parameters comprise wavelength values or polarizations of an incident radiation.

30. The method of clause 28, wherein at least one metrology target is designed for a different illumination parameter.

31. The method of clause 28, wherein at least one metrology target is designed for a different process stack.

32. The method of clause 28, wherein at least one metrology target is designed for different wavelengths or polarizations of an incident radiation.

33. A metrology target, comprising: a plurality of metrology targets disposed at different locations on a substrate by a manufacturing process, wherein each metrology target comprises at least first and second metrology sub-targets that are different in design.

34. The metrology target of clause 33, wherein the first and second metrology sub-targets are designed for different process stacks.

35. The metrology target of clause 33, wherein the first and second metrology sub-targets are designed for different illumination parameters.

36. The metrology target of clause 35, wherein the illumination parameters comprise wavelength values or polarizations of an incident radiation.

Although specific reference may have been made above to the use of embodiments in the context of optical lithography, it will be appreciated that an embodiment of the invention may be used in other applications, for example imprint lithography, and where the context allows, is not limited to optical lithography. In imprint lithography, a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

Further, although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

The descriptions above are intended to be illustrative, not limiting. Thus, it will be apparent to one skilled in the art that modifications may be made to the invention as described without departing from the scope of the claims set out below. For example, one or more aspects of one or more embodiments may be combined with or substituted for one or more aspects of one or more other embodiments as appropriate. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance. The breadth and scope of the invention should not be limited by any of the above-described exemplary embodiments, but should be defined only in accordance with the following claims and their equivalents.

What is claimed is:

1. A method comprising:
   producing a plurality of metrology targets by a manufacturing process, the plurality of metrology targets having been designed for different wavelengths or polarizations of an incident radiation or process stacks;
   measuring light scattered by the plurality of metrology targets;
   determining a modification value for each metrology target; and
   determining a multiplication factor for each metrology target based on its corresponding modification value.

2. The method of claim 1, wherein the determining the multiplication factors comprises determining a sum of the multiplication factors multiplied by their corresponding modification values.

3. The method of claim 2, wherein the determining the multiplication factors further comprises adjusting the multiplication factors such that the sum is maximized.

4. The method of claim 1, wherein the modification values are target coefficients or overlay errors of the plurality of metrology targets.

5. The method of claim 1, wherein the modification values are stack sensitivity values of the plurality of metrology targets.

6. The method of claim 1, further comprising:
   determining lithographic process parameters using the modification value and the multiplication factor for each metrology target in the plurality of metrology targets, wherein the lithographic process parameters are overlay values.

7. The method of claim 1, wherein the metrology parameters comprise material choice, critical dimension, sub-segmentation, or sidewall angle.

8. The method of claim 1, wherein the plurality of metrology targets comprise multi-layer periodic structures.

9. The method of claim 8, wherein the metrology parameters of the multi-layer periodic structures comprise pitch, duty cycle of lines and spaces, height, or width.

* * * * *